(12) United States Patent
Miura et al.

(10) Patent No.: US 7,108,694 B2
(45) Date of Patent: Sep. 19, 2006

(54) HEAT-EMITTING TREATMENT DEVICE

(75) Inventors: Keisuke Miura, Hachioji (JP); Norihiko Hareyama, Hino (JP)

(73) Assignee: Olympus Corporation, Tokyo (JP)

( * ) Notice: Subject to any disclaimer, the term of this patent is extended or adjusted under 35 U.S.C. 154(b) by 263 days.

(21) Appl. No.: 10/701,927

(22) Filed: Nov. 5, 2003

(65) Prior Publication Data

US 2004/0092923 A1    May 13, 2004

(30) Foreign Application Priority Data

Nov. 8, 2002  (JP) ............................. 2002-325815
Nov. 8, 2002  (JP) ............................. 2002-325816

(51) Int. Cl.
*A61B 18/04* (2006.01)
(52) U.S. Cl. ............................. 606/31; 606/27; 606/28; 606/29
(58) Field of Classification Search ............. 606/27–31
See application file for complete search history.

(56) References Cited

U.S. PATENT DOCUMENTS

| | | | |
|---|---|---|---|
| 3,826,263 A | | 7/1974 | Cage et al. |
| 4,031,898 A | * | 6/1977 | Hiltebrandt et al. ......... 606/31 |
| 4,196,734 A | * | 4/1980 | Harris ......................... 606/31 |
| 4,219,025 A | * | 8/1980 | Johnson ...................... 606/31 |
| 4,654,024 A | * | 3/1987 | Crittenden et al. ........... 606/28 |
| 5,451,224 A | * | 9/1995 | Goble et al. .................. 606/48 |
| 5,573,533 A | * | 11/1996 | Strul ........................... 606/34 |
| 5,810,811 A | * | 9/1998 | Yates et al. ................... 606/50 |
| 6,235,027 B1 | * | 5/2001 | Herzon ........................ 606/51 |
| 2003/0208201 A1 | * | 11/2003 | Iida et al. .................... 606/51 |

* cited by examiner

*Primary Examiner*—Michael Peffley
*Assistant Examiner*—Alex B. Toy
(74) *Attorney, Agent, or Firm*—Scully,Scott,Murphy & Presser, P.C.

(57) ABSTRACT

Treatment equipment for treating body tissue comprises heater elements which are heated by electric power supplied from an electric power supply circuit, and the heat of the heater elements is provided to the body tissue through a heat transmitting member. The state of thermal connection between the heater elements and the heat transmitting member is determined by a determining device for determining the thermal connection state.

29 Claims, 20 Drawing Sheets

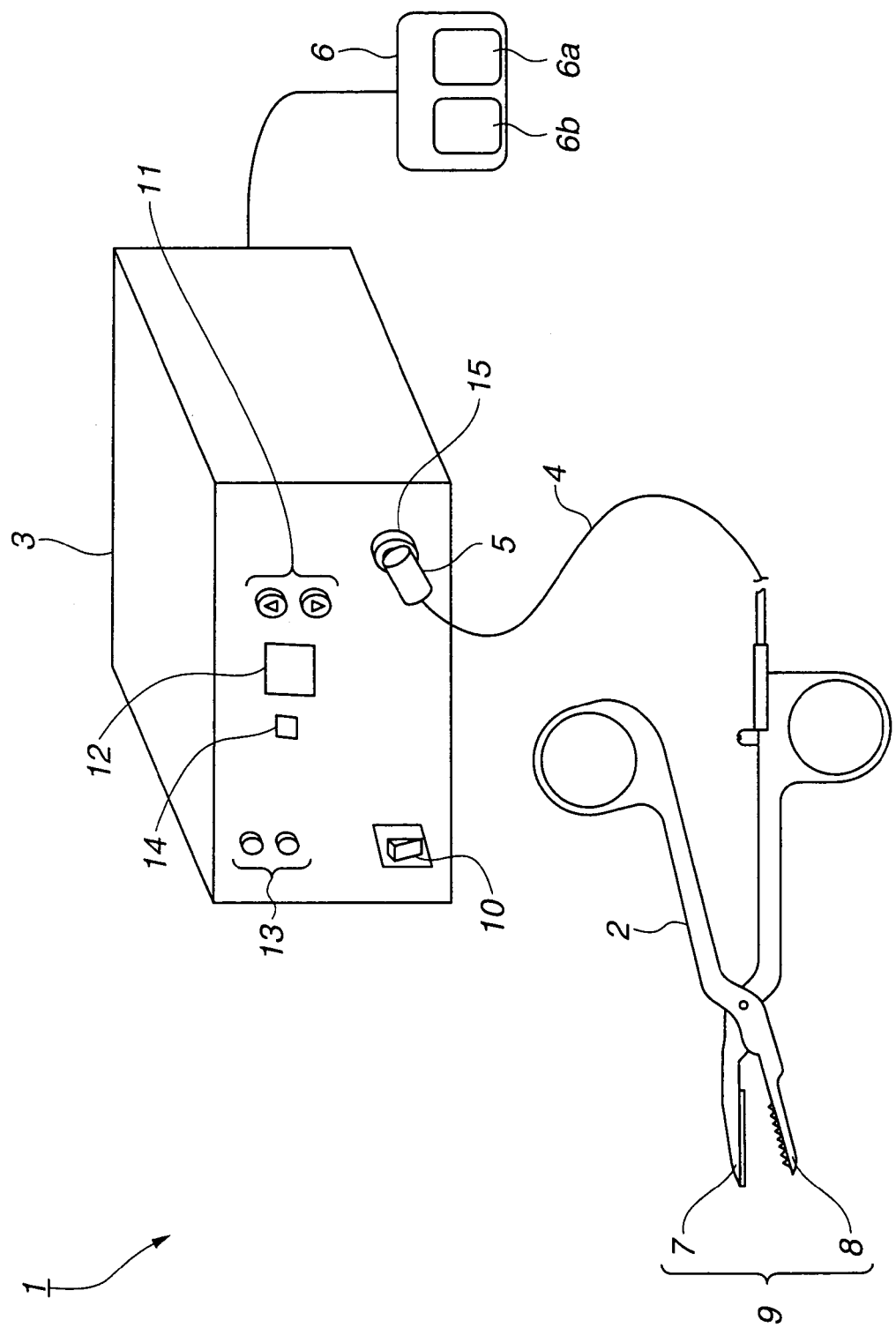

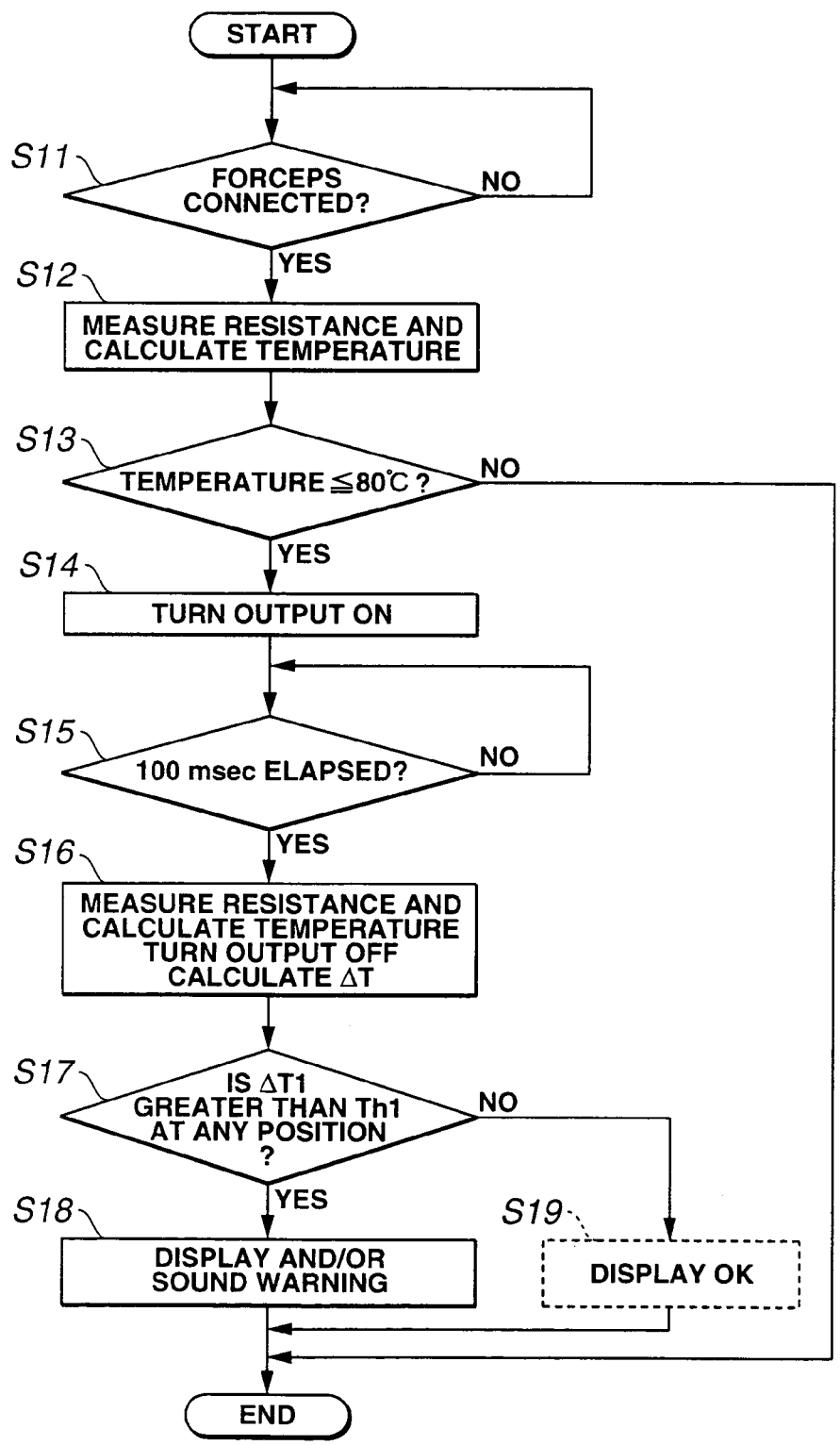

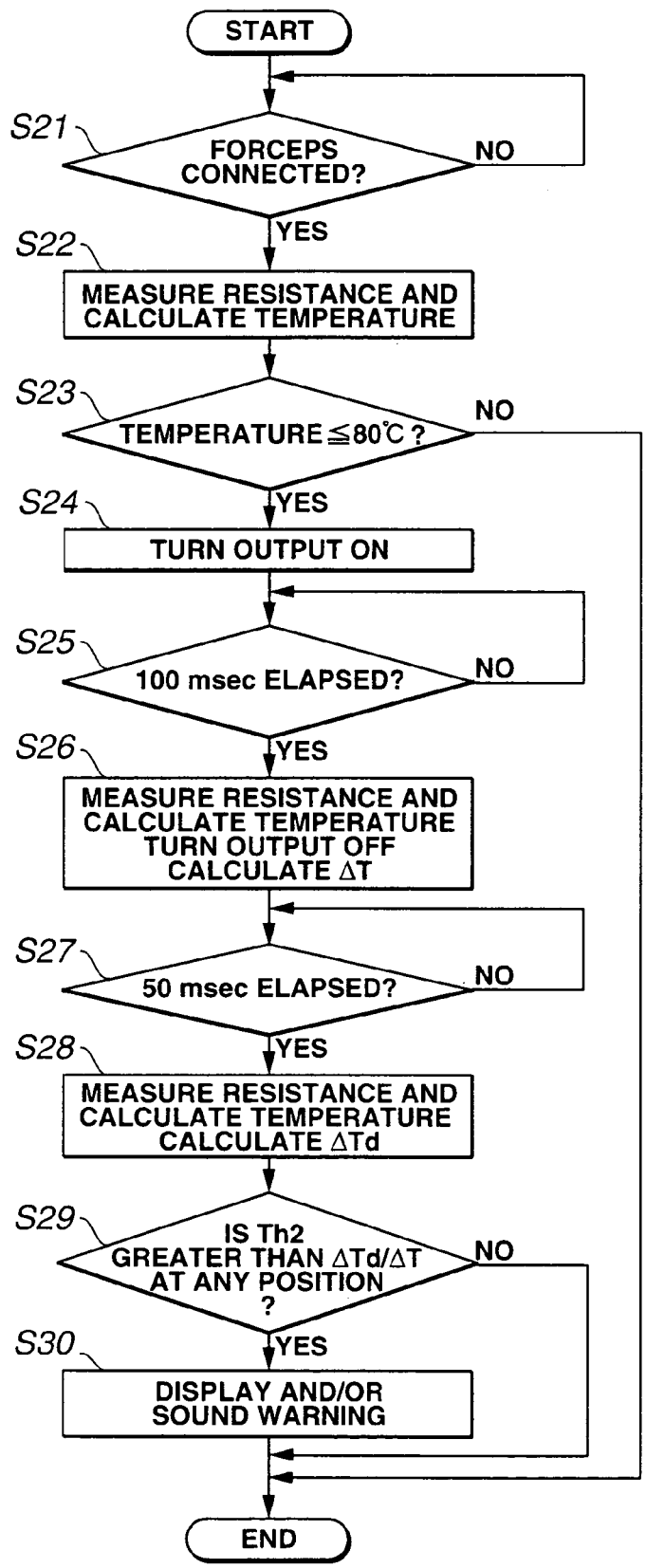

HEAT-EMITTING TREATMENT DEVICE

This application claims benefit of Japanese Application Nos. 2002-325815 filed on Nov. 8, 2002 and 2002-325816 filed on Nov. 8, 2002, the contents of which are incorporated by this reference.

BACKGROUND OF THE INVENTION

1. Field of the Invention

The present invention relates to a heat-emitting treatment device for performing coagulation and incision of body tissue with heat, and particularly relates to a heat-emitting treatment-device having functions for detecting a state of connecting with a transmitting member for transmitting the heat of heat-generating elements to body tissue.

2. Description of the Related Art

In recent years, electric treatment devices have come to be used as diagnostic and treatment devices in the field of medicine. Such electric treatment devices use heat-emitting elements for treatment such as incision, cauterizing, suturing, etc., of body tissue. The heat-emitting treatment devices transmit heat generated from a heat-emitting portion to the part of the body tissue to be treated, and perform coagulation or incision of body tissue with the transmitted heat.

The state of application of heat to the body tissue must be controlled in order to perform coagulation or incision thereby, and a technique wherein the heat-emitting electric power supplied to the heat-emitting portion is detected so as to control the amount of heat emitted from the heat-emitting portion is commonly used. However, the results of coagulation differ according to the size, thickness, etc., of the body tissue to be coagulated.

An electric power source for a heat-emitting treatment device has been proposed which controls subsequent supply of heat-emitting electric power according to the amount of heat-emitting electric power supplied until the temperature of the heat-emitting portion reaches a predetermined value, or the amount of time of the heat-emitting electric power being supplied, so as to enable suitable coagulation processing corresponding to the state of the body tissue (e.g., Japanese Unexamined Patent Application Publication No. 2001-269352).

Also, Japanese Examined Patent Application Publication No. 53-9031 discloses coagulation/incision forceps with a heat-emitting treatment device wherein multiple heater segments, which are heat-emitting elements, provided along the a thin ceramic incision edge portion, formed suitable for incision. Each of the multiple heater segments are formed electrically separated, so that the body tissue can be subjected to heat application treatment with the same temperature from the multiple heater segments.

With such known coagulation/incision forceps, the heat generated at the heater segments is transmitted to the body tissue by a metal blade directly in contact with the body tissue, and the heater segments and the metal blade are connected by soldering so that the emitted heat of the heater segments can be efficiently transmitted to the metal blade.

SUMMARY OF THE INVENTION

It is an object of the present invention to provide a new and improved heat-emitting treatment device.

To this end, a heat-emitting treatment device according to the present invention comprises heater elements for emitting heat to treat body tissue and an electric power supplying circuit for supplying electric power so that the heater elements emit heat. The heat-emitting treatment device also comprises a heat-transmitting member connected with the heater elements so as to provide the heat from the heater elements, heated by supplying electric power thereto, to the body tissue, and a determining device for determining the connection state of the heater elements and the heat-transmitting member.

BRIEF DESCRIPTION OF THE DRAWINGS

FIGS. 1 through 5 relate to a first embodiment of the present invention, wherein FIG. 1 is a schematic diagram illustrating the overall configuration of a heat-emitting treatment device according to a first embodiment;

FIG. 3 is a block diagram illustrating the configuration of the main device unit of the heat-emitting treatment device;

FIG. 4 is an explanatory diagram for describing the change in heat mission temperature of the heat-emitting elements of the heat-emitting treatment device;

FIG. 5 is a flowchart illustrating the determination actions of the thermal connection at the heat-emitting treatment portion in the heat-emitting treatment device;

FIGS. 6 and 7 relate to a second embodiment of the present invention, wherein FIG. 6 is an explanatory diagram for describing the change in heat mission temperature of the heat-emitting elements of the heat-emitting treatment device according to the second embodiment;

FIG. 7 is a flowchart illustrating the determination operations for thermal connection of the heat-emitting treatment unit by the main device unit;

FIGS. 8 and 9 relate to a third embodiment of the present invention, wherein FIG. 8 is an explanatory diagram for describing the change in heat mission temperature of the heat-emitting elements of the heat-emitting treatment device according to the third embodiment;

FIG. 9 is a flowchart illustrating the determination operations for thermal connection of the heat-emitting treatment unit by the main device unit;

FIGS. 10 and 11 relate to a fourth embodiment of the present invention, wherein FIG. 10 is an explanatory diagram for describing the change in heat mission temperature of the heat-emitting elements of the heat-emitting treatment device according to the fourth embodiment;

FIG. 11 is a flowchart illustrating the determination operations for thermal connection of the heat-emitting treatment unit by the main device unit;

FIGS. 12A through 13 relate to a fifth embodiment of the present invention, wherein FIG. 12A is a block diagram illustrating the configuration of the main device unit of the heat-emitting treatment device according to the fifth embodiment;

FIG. 13 is a flowchart illustrating the determination operations for thermal connection of the heat-emitting treatment unit by the main device unit;

FIGS. 14 through 23 relate to a sixth embodiment of the present invention, wherein FIG. 14 is a block diagram illustrating the overall configuration of the heat-emitting treatment device according to the sixth embodiment;

FIG. 16 is a plan view illustrating the configuration of coagulation/incision forceps;

FIGS. 18A and 18B illustrate the configuration of the treatment portion of the coagulation/incision forceps, wherein FIG. 18A is a cross-sectional view perpendicular to the plane of the drawing in FIG. 13, and FIG. 18B is a cross-sectional view parallel to the plane of the drawing in FIG. 13;

FIG. 19 is a block diagram illustrating the internal configuration of the main device unit;

FIG. 20 is an explanatory diagram for describing the electric power applied to the heat-generating elements in the event of normal connection of the heat-emitting treatment unit of the coagulation/incision forceps;

FIG. 21 is an explanatory diagram for describing the electric power applied to the heat-generating elements in the event of abnormal connection of the heat-emitting treatment unit of the coagulation/incision forceps;

FIG. 22 is a flowchart describing the determining processing operations for the connection state of the heat-emitting treatment unit of the coagulation/incision forceps; and FIG. 23 is a flowchart describing the determining processing operations for the connection state of the heat-emitting treatment unit of the heat-emitting treatment device according to a modification of the sixth embodiment.

DESCRIPTION OF THE PREFERRED EMBODIMENTS

Figure 2A:
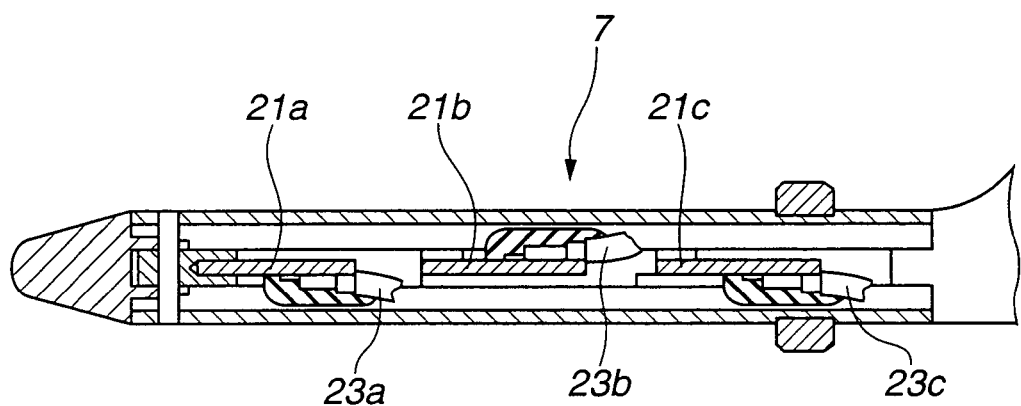
FIGS. 2A and 2B are cross-sectional views illustrating the configuration of a tissue gripping portion of coagulating incision forceps.

Embodiments of the present invention will now be described with reference to the drawings.

First Embodiment

The first embodiment of the present invention will be described with reference to FIGS. 1 through 5. As shown in FIG. 1 a heat-emitting treatment device 1 according to the first embodiment comprises coagulation/incision forceps 2 serving as heat-emitting treatment equipment provided with heat-emitting elements (heater elements), for generating heat to perform treatment such as coagulation and incision, and a heat-emitting treatment device main unit (hereafter referred to simply as "main device unit") 3 for supplying heat-emitting electric power to the coagulation/incision forceps 2 so as to generate heat thereby.

The coagulation/incision forceps 2 have at the tip portion thereof a heat-emitting treatment unit 7 for grasping the body tissue and performing coagulation and incision with heat, and an elastic receiving unit 8 having elasticity which opposes the heat-emitting treatment unit 7. The heat-emitting treatment unit 7 and the elastic receiving unit 8 together make up a tissue grasping unit 9 for grasping body tissue. The heat-emitting treatment unit 7 and the elastic receiving unit 8 making up the tissue grasping unit 9 can be opened and closed by turning or a common pivot behind the tips thereof. A cable 4 extends from the rear end of an operating portion at the rear of the heat-emitting treatment unit 7 which a technician or the like holds and operates.

The device main unit 3 generates electric power for emitting heat in order to perform coagulation and incision, which is supplied to the heat-emitting treatment unit 7 of the coagulation/incision forceps 2 through the cable 4. On the front panel of the device main unit 3 is provided an electric power switch 10 for turning the commercial power driving the device main unit 3 on and off, and output settings switches 11 for setting the output value of the heat mission electric power to be supplied to the coagulation/incision forceps 2 from the device main unit 3.

Also provided on the front panel are an output settings display unit 12 for displaying the output value set with the output settings switches 11, and error display unit 13 for displaying damage or thermal connection errors regarding the heat-emitting treatment unit 7 of the coagulation/incision forceps 2, and output display unit 14 for indicating whether or not output is being made form the device main unit 3 to the coagulation/incision forceps 2, and a forceps connector 15 whereby a cable connector 5 at the end of the cable 4 of the coagulation/incision forceps 2 is detachably connected, through which the heat mission electric power is output.

While the error display unit 13 for notifying an error status by display is used for displaying problems with thermal connection based on the determination results of thermal connection, this may also be used for indicating suitable determination results as well.

Also, a foot switch 6 is connected to the rear face of the device main unit 3, and is operated to control instructions of supplying electric power for heat emission to the coagulation/incision forceps 2. The foot switch 6 comprises a maximum output switch 6a for instructing maximum output, and a set output switch 6b for instructing output of a value set with the output settings switches 11. The set output and the maximum output are correlated to the heat mission temperature of the heat-emitting treatment unit 7.

Figure 2B:
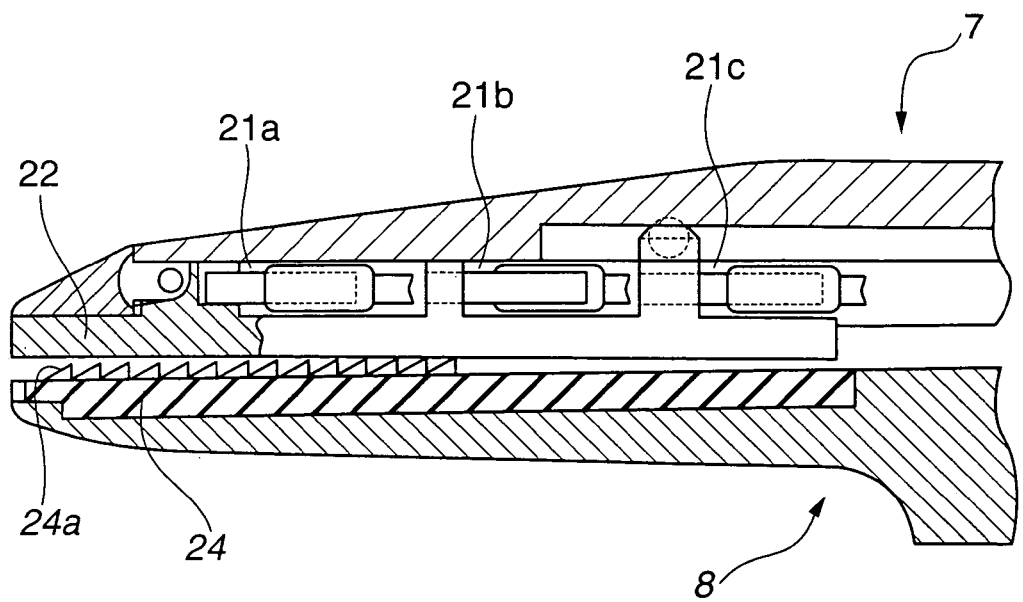

Next, the detailed configuration of the tissue grasping unit 9 of the coagulation/incision forceps 2 will be described in detail with reference to FIGS. 2A and 2B. FIG. 2A is a cross-sectional view of the heat-emitting treatment unit 7 of the tissue grasping unit 9, perpendicular to the plane of the drawing, and FIG. 2B is a cross-sectional view of the heat-emitting treatment unit 7 of the tissue grasping unit 9 and the elastic receiving unit 8, parallel to the plane of the drawing in FIG. 1.

Multiple heat-generating elements 21a through 21c are disposed within the heat-emitting treatment unit 7 of the tissue grasping unit 9. The multiple heat-generating elements 21a through 21c have respective element cables 23a through 23c connected thereto. The element cables 23a through 23c are contained within the cable 4.

Each of the heat-generating elements 21a through 21c are mechanically and thermally connected with a heat transmitting member 22 formed of a member with excellent thermal conductivity. More specifically, the generally plate-shaped heat transmitting member 22 is provided on the face of the heat-emitting treatment unit 7 which faces the elastic receiving unit 8, and the heat-generating elements 21a through 21c are provided on the other side of the transmitting member 22 as to the elastic receiving unit 8, such that the heat-emitting faces of the heat-generating elements 21a through 21c are connected to the heat transmitting member 22.

The heat-generating elements 21a through 21c are formed of resistor heating elements for example, and generate heat (exhibit increase in temperature) due to heat-generating electric power being supplied thereto through the element cables 23a through 23c contained in the cable 4 connected to the forceps connector 15 of the device main unit 3. The heat emitted from the heat-generating elements 21a through 21c is transmitted to the body tissue through the heat transmitting member 22, thereby enabling the body tissue to be heated and coagulation and incision treatment to be carried out.

On the other hand, an elastic member 24 is provided on the face opposing the heat transmitting member 22 of the heat-emitting treatment unit 7, with non-slip formations 24a formed on the surface of the elastic member 24 so as to prevent slipping of body tissue held between the elastic member 24 and the heat-emitting treatment unit 7, formed with saw-tooth shapes or the like.

A technician performing treatment performs operations for heat mission driving of the heat-generating elements 21a through 21c in a state of body tissue being held between the heat transmitting member 22 of the heat-emitting treatment unit 7 and the elastic member 24 of the elastic receiving unit 8, whereby the heat from the heat-generating elements 21a through 21c is transmitted to the body tissue through the heat transmitting member 22, thus enabling coagulation and incision treatment of the body tissue with the transmitted heat.

Note that while the example shown has three heat-generating elements 21a through 21c provided to the heat-emitting treatment unit 7, but the number of heat-generating elements 21, and the shape and dimensions of the heat transmitting member 22, may be changed in various ways according to the body tissue being treated with the coagulation/incision forceps 2.

Next, the internal configuration of the device main unit 3 will be described with reference to FIG. 3. The device main unit 3 comprises output units 31a through 31c serving as electric power supplying means to supply (output) electric power for heat emission to each of the heat-generating elements 21a through 21c provided to the heat-emitting treatment unit 7 of the coagulation/incision forceps 2 which are connected via the cable 4 having the cable connector 5 connected to the forceps connector 15, temperature measuring units 32a through 32c for measuring the temperature of the heat generated by the heat-generating elements 21a through 21c connected to the respective output units 31a through 31c, and a control unit 33 for controlling the driving of the temperature measuring units 32a through 32c, the output units 31a through 31c, and a later-described operating/display unit 34.

The operating/display unit 34 is configured of an electric power switch 10, output settings switches 11, an output settings display unit 12, an error display unit 13, and an output display unit 14, each provided on the front panel, and a foot switch 6.

Figure 3:
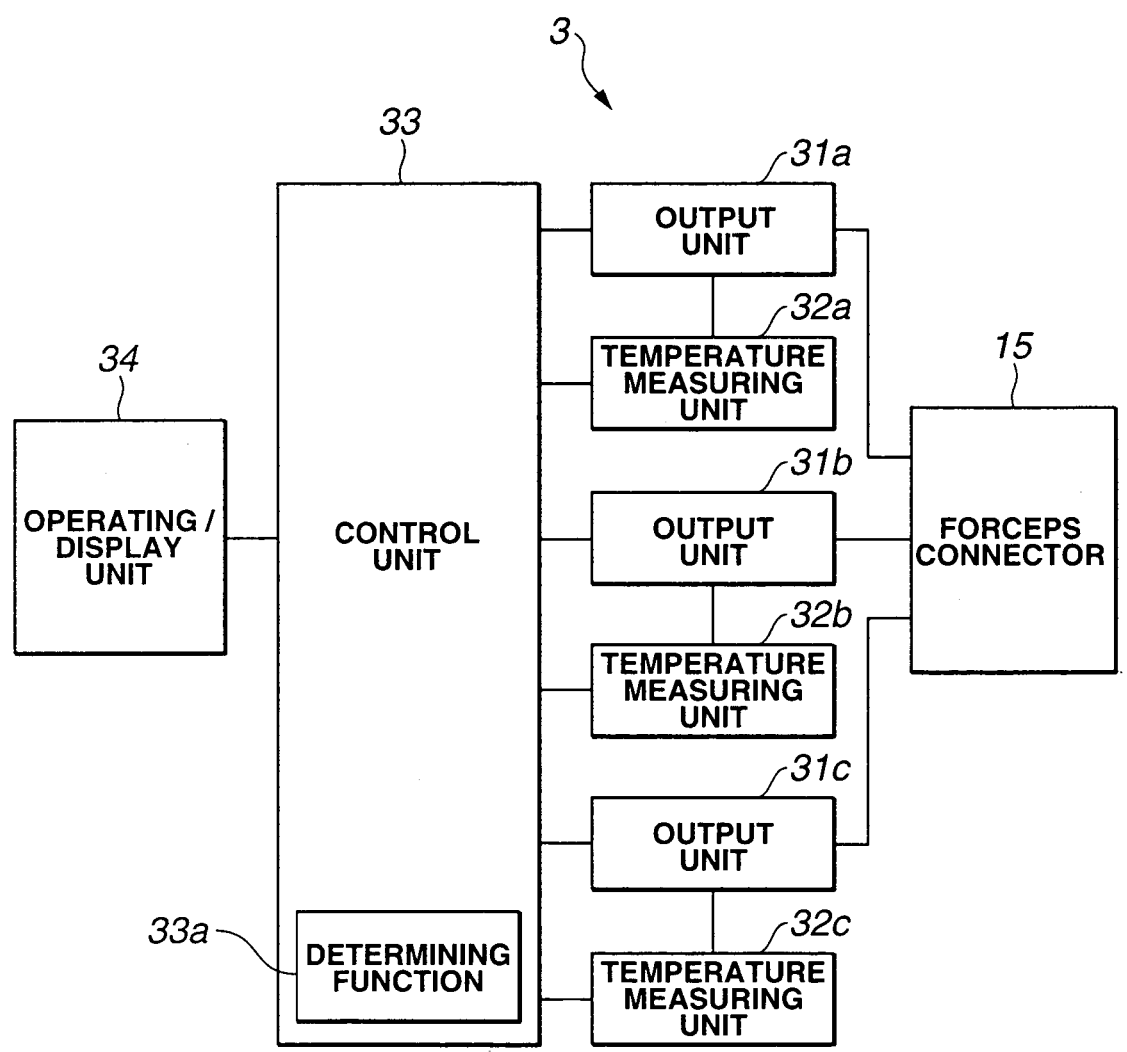

The control unit 33 controls driving of the display units 12, 13, and 14, according to input operations of the switches 6, 10, and 11, of the operating/display unit 34, controls output of the heat mission electric power from the output units 31a through 31c, and determines and controls the thermal connection state of the heat-generating elements 21a through 21c and the heat transmitting member 22 based on the temperature of heat emission measured with the temperature measuring units 32a through 32c (note that in FIG. 3, this determination is listed as a determining function 33a).

Accordingly, upon the user connecting the cable connector 5 of the coagulation/incision forceps 2 to the forceps connector 15 of the device main unit 3, and turning the electric power switch 10 on, the control unit 33 begins to operate and sets the amount of electric power for heat emission to be output from the output units 31a through 31c according to operations made with the output settings switches 11, and also displays the set electric power on the output settings display unit 12.

In this state, turning the foot switch 6 on causes the control unit 33 to drive the output units 31a through 31c and output the set heat emission electric power to the respective heat-generating elements 21a through 21c of the heat-emitting treatment unit 7, and also control the driving of the temperature measuring units 32a through 32c so as to measure the temperature of heat emission of the respective heat-generating elements 21a through 21c of the heat-emitting treatment unit 7.

This temperature measurement is performed by measuring the voltage and electric current of the heat emission electric power supplied to each of the heat-generating elements 21a through 21c, and dividing the voltage by the electric current, thereby calculating the resistance of each of the heat-generating elements 21a through 21c. The heat emission temperature and resistance of the heat-generating elements 21a through 21c are proportionate, so the resistance calculated from the measured voltage and current can be converted into the temperature of the heat generated.

Also, the control unit 33 effects control such that a minute electric power, lower than that which would enable coagulation or incision with the heat-generating elements 21a through 21c, is supplied from the output units 31a through 31c so as to measure the resistance of the heat-generating elements 21a through 21c of the heat-emitting treatment unit 7 prior to starting heat emission. Also, the current and voltage measured at the temperature measuring units 32a through 32c under the minute electric power are used to detect the room temperature of the heat-generating elements 21a through 21c prior to starting heat emission.

Also, operating the foot switch 6 causes the control unit 33 to control driving of the output units 31a through 31c so as to supply heat emission electric power to the heat-generating elements 21a through 21c, and also control the output values of the output units 31a through 31c so as to maintain the temperature of heat generation set for the heat-generating elements 21a through 21c.

Figure 4:
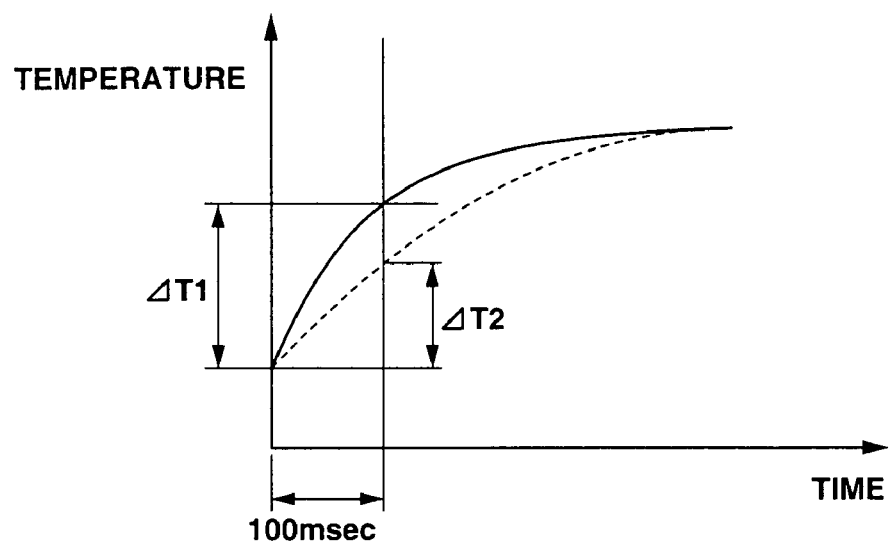

The change in temperature of a heat-generating element 21 (representing the heat-generating elements 21a through 21c), calculated from the voltage value and current value measured by a temperature measuring unit 32 (representing the temperature measuring units 32a through 32c) under application of heat emission electric power to the heat-generating element 21 from the output unit 31 of the main device unit 3 of a heat-emitting treatment device 1 configured thus, will be described with reference to FIG. 4. FIG. 4 illustrates the change in temperature of the heat generated by the heat-generating element 21 over time during which heat emission electric power is supplied thereto. The horizontal axis represents time, and the vertical axis represents the generated temperature.

In the event that the thermal connection of the heat-generating element 21 and the heat transmitting member 22 is good, the heat generated at the heat-generating element 21 is effectively conducted to the heat transmitting member 22 and dissipated, so a relatively gradual increase in temperature is exhibited, as indicated by the dotted line in FIG. 4.

On the other hand, in the event that the thermal connection of the heat-generating element 21 and the heat transmitting member 22 is poor, the heat generated at the heat-generating element 21 is not effectively conducted to the heat transmitting member 22 so conduction and dissipation is inefficient, and a steep increase in temperature is exhibited, as indicated by the solid line in FIG. 4.

Thus, in the event that the thermal connection state of the heat-generating element 21 and the heat transmitting member 22 is poor, the heat generated by the heat-generating element 21 is not effectively conducted to the heat transmitting member 22 after supply of electric power starts, and the temperature of the heat-generating element 21 alone rapidly rises. That is to say, the temperature change over a predetermined amount of time starting immediately after supply of the heat emission electric power is started, is unaffected by the shape of the heat transmitting member 22 and whether or not body tissue is present, but rather depends only on the state of thermal connection between the heat-generating element 21 and the heat transmitting member 22.

Thus, the control unit 33 can determine the connection state between the heat-generating element 21 and the heat transmitting member 22, using information of the change in temperature of the heat-generating element 21 within a predetermined amount of time starting immediately after supply of the heat emission electric power is started.

Figure 5:
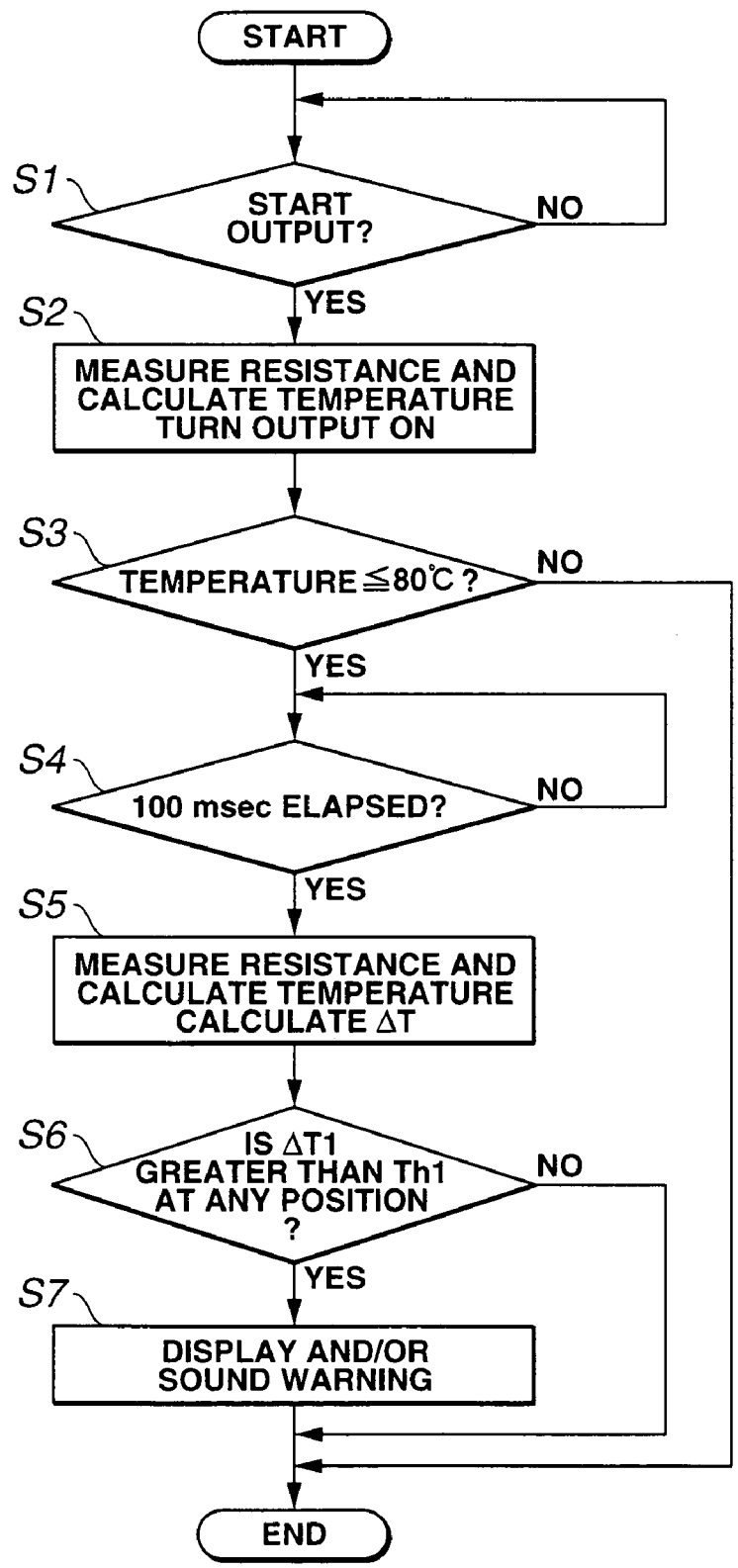

The process of the control unit 33 determining the connection state between the heat-generating element 21 and the heat transmitting member 22 by measuring the change in temperature of the heat-generating element 21 within a predetermined amount of time starting immediately after supply of the heat emission electric power is started will be described with reference to FIG. 5.

Note that with the first embodiment, processing for determining the thermal connection of the heat-emitting treatment unit 7 of the coagulation/incision forceps 2 is performed each time thermal emission electric power is supplied to the coagulation/incision forceps 2 from the main device unit 3.

First, preparation for the coagulation/incision processing is performed, such as connecting the cable connector 5 of the coagulation/incision forceps 2 to the forceps connector 15 of the device main unit 3, turning the electric power switch 10 on, setting the heat emission electric power value to be supplied to the heat-emitting treatment unit 7 of the coagulation/incision forceps 2 with the output settings switches 11, and so forth. Upon these preparations being completed, in step Si the control unit 33 enters a standby state for input of instructions from the foot switch 6 to start output of heat emission electric power.

Upon the foot switch 6 being operated to instruct output of heat emission electric power, in step S2 the control unit 33 drives the temperature measuring units 32a through 32c to calculate the resistance value of the heat-generating elements 21a through 21c based on the minute electric power supplied to the heat-generating elements 21a through 21c from the output units 31a through 31c, and calculate the temperature of heat emission from the resistance value, thereby measuring the room temperature of each of the heat-generating elements 21a through 21c before starting coagulation/incision.

Upon the temperature measurement of the heat-generating elements 21a through 21c ending, the control unit 33 drives the output units 31a through 31c to supply heat emission electric power for coagulation and incision to each of the heat-generating elements 21a through 21c. Along with supplying of the heat emission electric, the control unit 33 starts a time count of unshown timer functions for measuring time.

Next, in step S3, the control unit 33 determines whether or not the temperature of the heat-generating elements 21a through 21c measured in step S2 before starting coagulation/incision is equal to or lower than the standard temperature 80° C. In the event that the results of determination show that any one of the heat-generating elements 21a through 21c exceeds 80° C., this means that the effects of afterheat of the previous treatment are too great to determine the connection state, so the determining operations of the connection state between the heat-generating element 21 and heat transmitting member 22 are ended. That is, this step S3 serves to determine whether or not the conditions for determining the connection state are satisfactory.

The standard temperature 80° C. with which the temperature is compared has been obtained by experiment, but the present invention is not restricted to this value, and other values may be used as long as the connection state between the heat-generating element 21 and heat transmitting member 22 can be determined.

In the event that the measured temperature before starting coagulation/incision is determined to be equal to or lower than 80° C. in step S3, the control unit 33 stands by in step S4 until 100 msec elapse on the timer count of the timer functions started at the time of starting the supply of heat emission electric power in step S2. This timer count of 100 msec has been obtained by experiment, but the present invention is not restricted to this value, and other values may be used as long as the value is a value wherein the temperature of heat emission reaches that for determining the connection state between the heat-generating element 21 and heat transmitting member 22.

Following 100 msec elapsing on the timer count in step S4, in step S5 the control unit 33 drives the temperature measuring units 32a through 32c again, and measures the generated temperature of the heat-generating elements 21a through 21c by calculating the resistance value of the heat-generating elements 21a through 21c based on the voltage and current values of the heat emission electric power supplied to the heat-generating elements 21a through 21c, and converting the resistance value into the temperature of heat emission.

The difference ΔT between the heat generation temperature of the heat-generating elements 21a through 21c measured in step S5, and the heat generation temperature of each of the heat-generating elements 21a through 21c measured in step S2 before starting coagulation/incision, is calculated. That is to say, ΔT1 or ΔT2 in FIG. 4 is calculated.

Next, in step S6, the control unit 33 compares the heat generation temperature difference ΔT calculated in step S5 with a preset predetermined temperature difference Th1. The predetermined temperature difference Th1 is a value experimentally obtained from various connecting states between the heat-generating element 21 and heat transmitting member 22, and serves as a reference value for determining whether or not the thermal connecting state of the heat-generating element 21 and heat transmitting member 22 is good.

In this step S6, in the event that the generation temperature differences ΔTa thorough ΔTc for each of the heat-generating elements 21a through 21c are all equal to or below the predetermined temperature difference Th1, the control unit 33 determines that the connection state between the heat-generating elements 21a through 21c and the heat transmitting member 22 is good, as indicated by the dotted line in FIG. 4, and the process of determining the thermal connecting state of the heat-generating element 21 and heat transmitting member 22 ends.

On the other hand, in the event that even one of the generation temperature differences ΔTa thorough ΔTc for the heat-generating elements 21a through 21c exceeds the predetermined temperature difference Th1, the control unit 33 determines that the connection state between the heat-generating element 21 and the heat transmitting member 22 is not good, as indicated by the solid line in FIG. 4, and the control unit 33 notifies the technician in step S7 of a poor thermal connecting state of the heat-generating element 21 and heat transmitting member 22 by driving the error display unit 13 on the main device unit 3 or driving an unshown warning sound emitting function, and the process of determining the thermal connecting state of the heat-generating element 21 and heat transmitting member 22 ends.

Note that even in the event that a poor connection between the heat-generating element 21 and heat transmitting member 22 is detected, the coagulation/incision forceps 2 do not become unusable, so an arrangement may be made wherein the control unit 33 continues to supply heat emission electric power from the output unit 31.

As described above, with the heat-emitting treatment device 1 according to the first embodiment of the present invention, whether or not the connection state between the heat-generating elements 21a through 21c and the heat transmitting member 22 is good is determined in a short time (100 msec) each time heat emission electric power is supplied from the main device unit 3 to the multiple heat-generating elements 21a through 21c of the coagulation/incision forceps 2, so the technician can be notified in a sure manner even in the event that thermal connection deterioration between the heat-generating element 21 and heat transmitting member 22 occurs during repetitive use.

Also, whether or not the thermal connection is good is determined by temperature rise over a short time, so whether or not the thermal connection of the heat-generating element 21 and heat transmitting member 22 is good can be judged in a precise manner, without being affected by the size and shape of the heat transmitting member 22.

Second Embodiment

Figure 6:
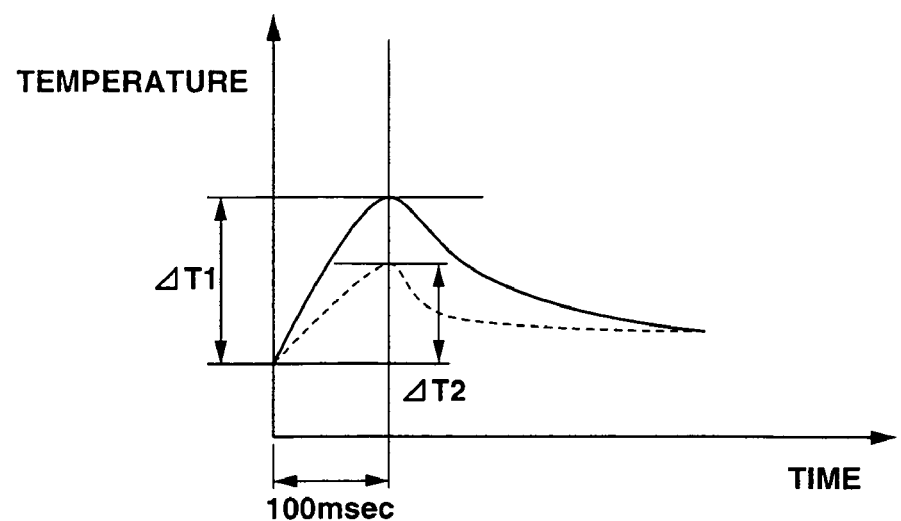

Next, the heat-emitting treatment device according to the second embodiment of the present invention will be described with reference to FIGS. 6 and 7. FIG. 6 is an explanatory diagram for describing the change in heat mission temperature of the heat-emitting elements of the heat-emitting treatment device according to the second embodiment of the present invention, and FIG. 7 is a flowchart illustrating the determination operations for thermal connection of the heat-emitting treatment unit by the main device unit.

The hardware configuration of the main device unit according to the second embodiment is the same as that of the main device unit according to the first embodiment, with the difference being the actions in determination processing by the control unit 33. More specifically, a program for stipulating the actions of an unshown CPU making up the control unit 33 differs from that of the first embodiment.

With the second embodiment, at the point that the coagulation/incision forceps 2 are connected to the main device unit 3, automatic determining processing is immediately performed regarding the connection state between the multiple heat-generating elements 21a through 21c provided to the heat-emitting treatment unit 7 of the coagulation/incision forceps 2 and the heat transmitting member 22.

As with FIG. 4 described above, in FIG. 6 the horizontal axis represents time, and the vertical axis represents the generated temperature of the heat-generating element 21. In the event that the thermal connection of the heat-generating element 21 and the heat transmitting member 22 is good, the heat generated at the heat-generating element 21 is effectively conducted to the heat transmitting member 22 and dissipated, so a relatively gradual increase in temperature is exhibited over a predetermined heat emission electric power supply period (a 100 msec period), as indicated by the dotted line in FIG. 6, and the temperature rapidly drops following stopping the supply of heat emission electric power (following the 100 msec period).

On the other hand, in the event that the thermal connection of the heat-generating element 21 and the heat transmitting member 22 is poor, the heat generated at the heat-generating element 21 is not effectively conducted to the heat transmitting member 22 so conduction and dissipation is inefficient, and a steep increase in temperature is exhibited over the predetermined heat emission electric power supply period (100 msec period), as indicated by the solid line in FIG. 6, and a long time is required for the temperature to drop following stopping the supply of heat emission electric power (following the 100 msec period), i.e., the temperature gradually drops.

The action of the processing routine, carried out by the control unit 33 of the main device unit 3 for determining the connection state of the heat-generating element 21 and the heat transmitting member 22 using the tendencies in temperature change of the heat-generating element 21 when heat emission electric power is supplied thereto for short periods, will be described with reference to the flowchart in FIG. 7.

Figure 12A:
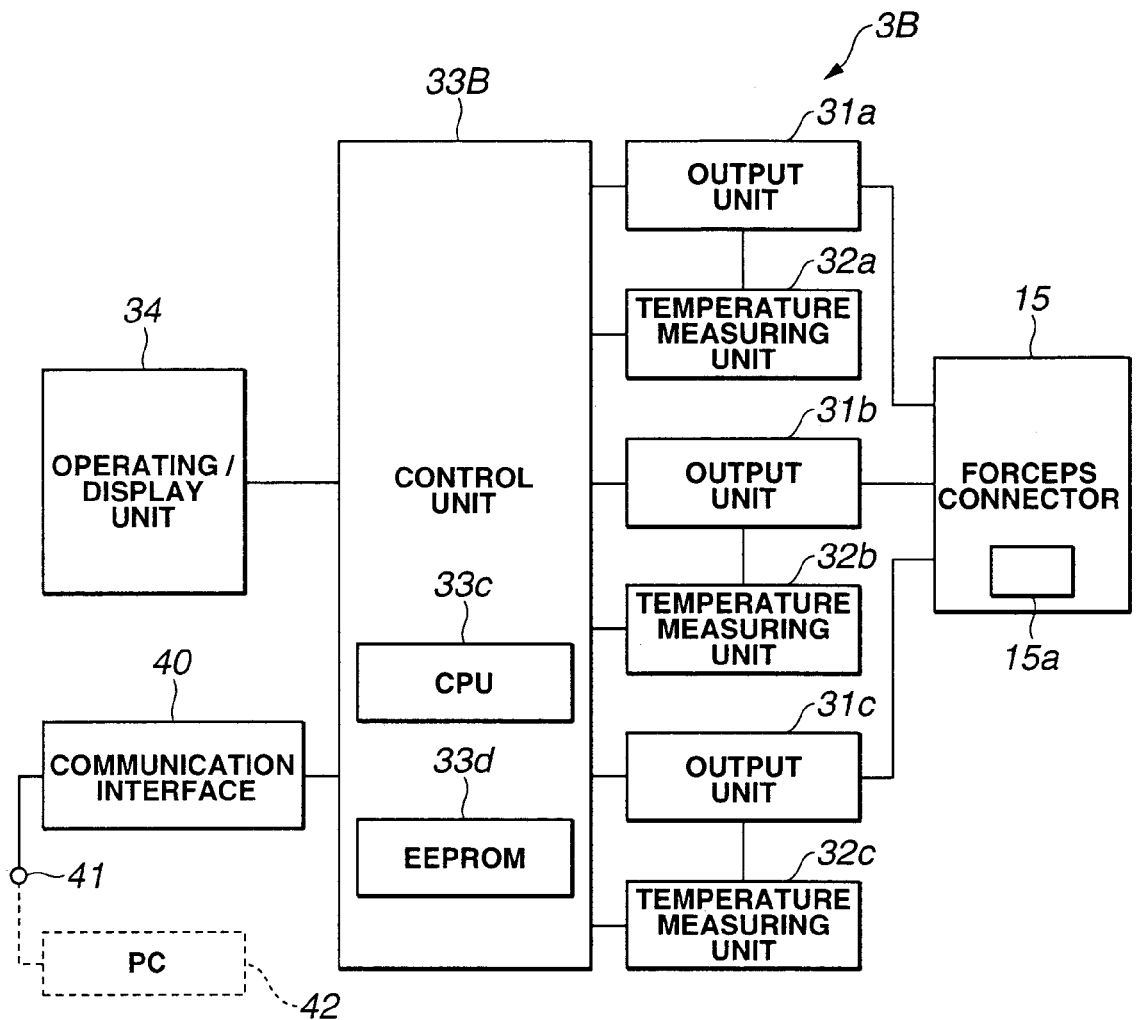
Figure 12B:
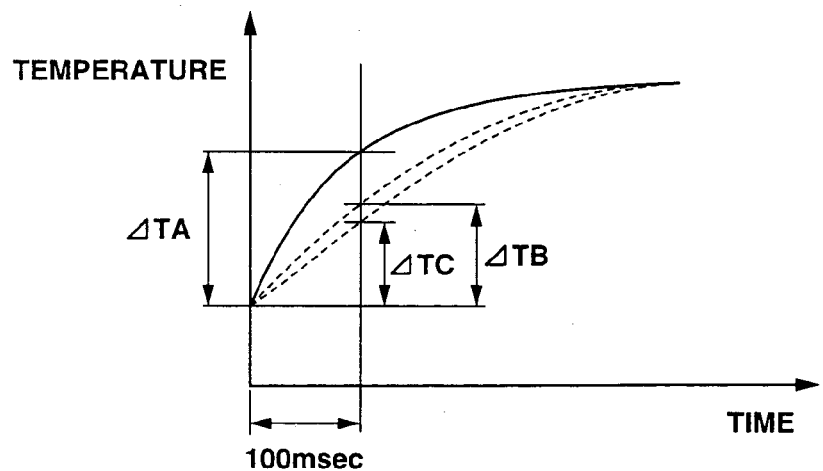
FIG. 12B is an explanatory diagram for describing the change in heat mission temperature of the heat-emitting elements.

Upon the electric power switch 10 of the main device unit 3 being turned on, in step S11 the control unit 33 enters a standby state for connection of the coagulation/incision forceps 2 to the forceps connector 15. Detection of connection of the coagulation/incision forceps 2 to the forceps connector 15 of the main device unit 3 is performed by unshown connection detection functions of the cable connector 5 of the coagulation/incision forceps 2 provided to the forceps connector 15, or by a method for detecting change in resistance upon connecting the coagulation/incision forceps 2 with a weak current, or the like (as shown in FIG. 12B to be described later, a connection detection unit 15a for the cable connector 5 may be provided to the forceps connector 15).

Upon the control unit 33 determining that the coagulation/incision forceps 2 have been connected in step S11, in step S12 the control unit 33 drives the temperature measuring units 32a through 32c to calculate the resistance value of the heat-generating elements 21a through 21c based on the minute electric power supplied to the heat-generating elements 21a through 21c from the output units 31a through 31c, and calculates the heat generation temperature from the resistance value, thereby measuring the room temperature of each of the heat-generating elements 21a through 21c before at the point of connection.

Next, in step S13, the control unit 33 determines whether or not the temperature of the heat-generating elements 21a through 21c measured in step S12 is equal to or lower than the standard temperature 80° C. In the event that the results of determination show that any one of the heat-generating elements 21a through 21c exceeds 80° C., this means that the effects of afterheat of the previous treatment are too great to determine the connection state, so the determining operations of the connection state between the heat-generating element 21 and heat transmitting member 22 are ended.

In the event that the temperature measured in step S13 is determined to be equal to or lower than 80° C., in step S14 the control unit 33 controls driving of the output units 31a through 31c to supply heat emission electric power to each of the heat-generating elements 21a through 21c, and also starts a time count of unshown timer functions for measuring time.

The control unit 33 then stands by in step S15 until 100 msec elapse on the timer count of the timer functions. Following 100 msec elapsing on the timer count in step S15, in step S16 the control unit 33 drives the temperature measuring units 32a through 32c again, and measures the generated temperature of the heat-generating elements 21a through 21c by calculating the resistance value of the heat-generating elements 21a through 21c based on the voltage and current values of the heat emission electric power supplied to the heat-generating elements 21a through 21c, and converting the resistance value into heat generation temperature. The control unit 33 then stops the output of the output units 31a through 31c so as to stop supply of the heat emission electric power to the heat-generating elements 21a through 21c.

Further, in step S16, the difference ΔT between the heat generation temperature of the heat-generating elements 21a through 21c measured in step S16, and the temperature of each of the heat-generating elements 21a through 21c measured in step S12, is calculated. That is to say, ΔT1 or ΔT2 in FIG. 6 is calculated.

Next, in step S17, the control unit 33 compares the heat generation temperature difference ΔT calculated in step S16 with a preset predetermined temperature difference Th1. In step S17, in the event that the heat generation temperature differences ΔTa thorough ΔTc for each of the heat-generating elements 21a through 21c are all equal to or below the predetermined temperature difference Th1, the control unit 33 determines that the connection state between the heat-generating elements 21a through 21c and the heat transmitting member 22 is good, as indicated by the dotted line in FIG. 6, and the process of determining the thermal connecting state of the heat-generating element 21 and heat transmitting member 22 ends. The control unit 33 may also effect control so as to display or notify the user that the connection state is good (OK), as indicated by step S19 drawn with a dotted line in FIG. 7.

On the other hand, in the event that even one of the heat generation temperature differences ΔTa thorough ΔTc for the heat-generating elements 21a through 21c exceeds the predetermined temperature difference Th1, the control unit 33 determines that the connection state between the heat-generating element 21 and the heat transmitting member 22 is not good, as indicated by the solid line in FIG. 6, and the control unit 33 notifies the technician in step S18 of a poor thermal connecting state of the heat-generating element 21 and heat transmitting member 22 by driving the error display unit 13 on the main device unit 3 or driving an unshown warning sound emitting function, and the process of determining the thermal connecting state of the heat-generating element 21 and heat transmitting member 22 ends.

As described above, with the heat-emitting treatment device according to the second embodiment of the present invention, the control unit 33 detects whether or not the connection state between the heat-generating elements 21a through 21c and the heat transmitting member 22 is good each time the coagulation/incision forceps 2 are connected to the main device unit 3, by effecting control to automatically supply heat emission electric power to the multiple heat-generating elements 21a through 21c of the coagulation/incision forceps 2 for a short time, so the technician can be notified of the state, whether good or poor, in a sure manner. Note that while the heat-generating element 21 of the coagulation/incision forceps 2 is heated for this determination, the heated state is short, so there is no effect on the body tissue.

Third Embodiment

Figure 8:
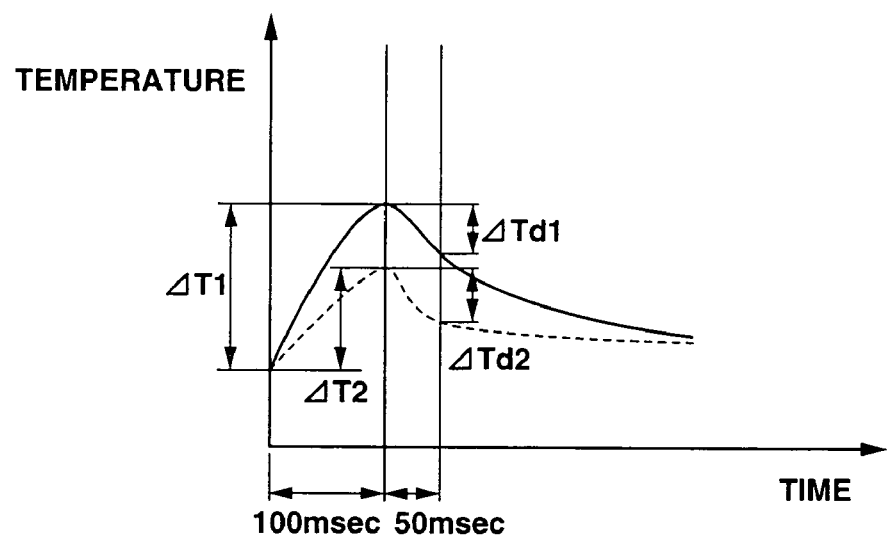

Next, the heat-emitting treatment device according to the third embodiment of the present invention will be described with reference to FIGS. 8 and 9. FIG. 8 is an explanatory diagram for describing the change in heat mission temperature of the heat-emitting elements of the heat-emitting treatment device according to the third embodiment of the present invention, and FIG. 9 is a flowchart illustrating the determination operations for thermal connection of the heat-emitting treatment unit by the main device unit.

The hardware configuration of the main device unit 3 according to the third embodiment is the same as that of the main device unit according to the first embodiment, with the difference being a processing program for performing automatic determining processing regarding the connection state between the multiple heat-generating elements 21a through 21c and the heat transmitting member 22 each time the coagulation/incision forceps 2 are connected, as with the second embodiment, and the automatic determining of the connected state is carried out in an even surer manner with this processing program.

As with FIG. 6 described above, in FIG. 8 the horizontal axis represents time, and the vertical axis represents the generated temperature of the heat-generating element 21, indicating the rise of heat generation temperature during heat emission electric power being supplied over a predetermined period (100 msec), and the fall of the temperature following stopping the supply of the heat emission electric power.

In the event that the thermal connection of the heat-generating element 21 and the heat transmitting member 22 is good, the heat generated at the heat-generating element 21 is effectively conducted to the heat transmitting member 22 and dissipated, so a relatively gradual temperature increase ΔT2 is exhibited over a predetermined heat emission electric power supply period (100 msec), as indicated by the dotted line in FIG. 8, and the ratio of the temperature drop ΔTd2 within a predetermined period (a 50 msec period) following stopping the supply of the heat emission electric power is great.

On the other hand, in the event that the thermal connection of the heat-generating element 21 and the heat transmitting member 22 is poor, the heat generated at the heat-generating element 21 is not effectively conducted to the heat transmitting member 22 so conduction and dissipation is inefficient, and a steep temperature increase ΔT1 is exhibited over the predetermined heat emission electric power supply period (100 msec period), as indicated by the solid line in FIG. 8, and the ratio of the temperature drop ΔTd1 within a predetermined period (a 50 msec period) following stopping the supply of the heat emission electric power is small. That is to say, the ratio of temperature rise to temperature drop differs according to the thermal connection state.

The action of the processing routine, carried out by the control unit 33 of the main device unit 3 for automatically determining the connection state of the heat-generating element 21 and the heat transmitting member 22 immediately after the coagulation/incision forceps 2 are connected to the main device unit 3 using this phenomenon will be described with reference to the flowchart in FIG. 9.

Upon the electric power switch 10 of the main device unit 3 being turned on, in step S21 the control unit 33 enters a standby state for connection of the coagulation/incision forceps 2 to the forceps connector 15. Detection of connection of the coagulation/incision forceps 2 to the forceps connector 15 of the main device unit 3 is performed by unshown connection detection functions of the cable connector 5 of the coagulation/incision forceps 2 provided to the forceps connector 15, or by a method for detecting change in resistance upon connecting the coagulation/incision forceps 2 with a weak current, or the like.

Upon the control unit 33 determining that the coagulation/incision forceps 2 have been connected in step S21, in step S22 the control unit 33 drives the temperature measuring units 32a through 32c to calculate the resistance value of the heat-generating elements 21a through 21c based on the minute electric power supplied to the heat-generating elements 21a through 21c from the output units 31a through 31c, and converts the resistance value into heat generation temperature, thereby measuring the room temperature of each of the heat-generating elements 21a through 21c before at the point of connection.

Next, in step S23, the control unit 33 determines whether or not the temperature of the heat-generating elements 21a through 21c measured in step S22 is equal to or lower than the standard temperature 80° C. In the event that the results of determination show that any one of the heat-generating elements 21a through 21c exceeds 80° C., this means that the effects of afterheat of the previous treatment are too great to determine the connection state, so the determining operations of the connection state between the heat-generating element 21 and heat transmitting member 22 are ended.

In the event that the temperature measured in step S23 is determined to be equal to or lower than 80° C., in step S24 the control unit 33 controls the output units 31a through 31c so as to supply heat emission electric power to each of the heat-generating elements 21a through 21c, and also starts a time count of unshown timer functions for measuring time.

The control unit 33 then stands by in step S25 until 100 msec elapse on the timer count of the timer functions. Following 100 msec elapsing on the timer count in step S25, in step S26 the control unit 33 drives the temperature measuring units 32a through 32c again, and measures the generated temperature of the heat-generating elements 21a through 21c by calculating the resistance value of the heat-generating elements 21a through 21c based on the voltage and current values of the heat emission electric power supplied to the heat-generating elements 21a through 21c, and converting the resistance value into heat generation temperature. The control unit 33 then stops driving the output units 31a through 31c so as to stop supply of the heat emission electric power to the heat-generating elements 21a through 21c.

Further, in step S26, the difference ΔT between the heat generation temperature of the heat-generating elements 21a through 21c measured in step S26, and the heat generation temperature of each of the heat-generating elements 21a through 21c measured in step S22, is calculated. That is to say, ΔT1 or ΔT2 in FIG. 8 is calculated.

Next, in step S27, the control unit 33 enters a standby state until another 50 msec elapses following the 100 msec in step S25. After the 50 msec elapsing in this standby state in step S27, in step S28 the control unit 33 drives the temperature measuring units 32a through 32c again, and measures the generated temperature of the heat-generating elements 21a through 21c by calculating the resistance value of the heat-generating elements 21a through 21c based on the voltage and current values of the weak heat emission electric power supplied to the heat-generating elements 21a through 21c, and converting the resistance value into temperature. The control unit 33 also calculates the difference ΔTd between the temperature of the heat-generating elements 21a through 21c measured in this step S27 and the temperature of each of the heat-generating elements 21a through 21c measured in step S26. That is to say, ΔTd1 or ΔTd2 is calculated, as shown in FIG. 8.

Further, the control unit 33 calculates the ratio ΔTd/ΔT between the rising temperature difference ΔT at the time of 100 msec elapsing under supply of heat emission electric power, and the temperature drop difference ΔTd at the point of 50 msec following stopping the heat emission electric power.

Next, in step S29, the control unit 33 compares the ratio ΔTd/ΔT between the rising heat generation temperature difference ΔT calculated in step S28 and the dropping temperature difference ΔTd, with a preset predetermined temperature ratio Th2 between a predetermined rising temperature ΔT and dropping temperature ΔTd. This predetermined temperature ratio Th2 is a value experimentally obtained from various connecting states between the heat-generating element 21 and heat transmitting member 22, and serves as a reference value for determining whether or not the thermal connecting state of the heat-generating element 21 and heat transmitting member 22 is good.

In step S29, in the event that all of the ratios ΔTda/ΔTa, ΔTdb/ΔTb, or ΔTdc/ΔTc, between the rising temperature differences ΔTa through ΔTc and the dropping temperature differences ΔTda through ΔTdc for the respective heat-generating elements 21a through 21c, is a predetermined temperature ratio Th2 or greater (ΔTd/ΔT >Th2), the control unit 33 determines that the connection state between the heat-generating elements 21a through 21c and the heat transmitting member 22 is good, as indicated by the dotted line in FIG. 8, and the process of determining the thermal connecting state of the heat-generating element 21 and heat transmitting member 22 ends. The control unit 33 may also effect control so as to display or notify the user by sound that the connection state is good, as with the case of step S19 in FIG. 7.

On the other hand, in the event that any one of the ratios ΔTda/ΔTa, ΔTdb/ΔTb, or ΔTdc/ΔTc, between the rising temperature differences ΔTa through ΔTc and the dropping temperature differences ΔTda through ΔTdc for the respective heat-generating elements 21a through 21c, is smaller than the predetermined temperature ratio Th2 (ΔTd/ΔT<Th2), the control unit 33 determines that there is a heat-generating elements 21a through 21c wherein the connection state with the heat transmitting member 22 is not good, as indicated by the solid line in FIG. 8, and the control unit 33 notifies the technician in step S30 of a poor thermal connecting state of the heat-generating element 21 and heat transmitting member 22 by driving the error display unit 13 on the main device unit 3 or driving an unshown warning sound emitting function, and the process of determining the thermal connecting state of the heat-generating element 21 and heat transmitting member 22 ends.

As described above, with the heat-emitting treatment device according to the third embodiment of the present invention, the control unit 33 precisely detects whether or not the connection state between the heat-generating elements 21a through 21c and the heat transmitting member 22 is good each time the coagulation/incision forceps 2 are connected to the main device unit 3, by effecting control to calculate the ratio between a rising temperature generated by automatically supplying heat emission electric power to the multiple heat-generating elements 21a through 21c for a short time, and the temperature drop following stopping the supply of heat emission electric power, and comparing this ratio with a reference value, so the technician can be notified of the state, whether good or poor, in a sure manner. Note that while the heat-generating element 21 of the coagulation/incision forceps 2 is heated for this determination, the heated state is short, so there is no effect on the body tissue.

Fourth Embodiment

Figure 10:
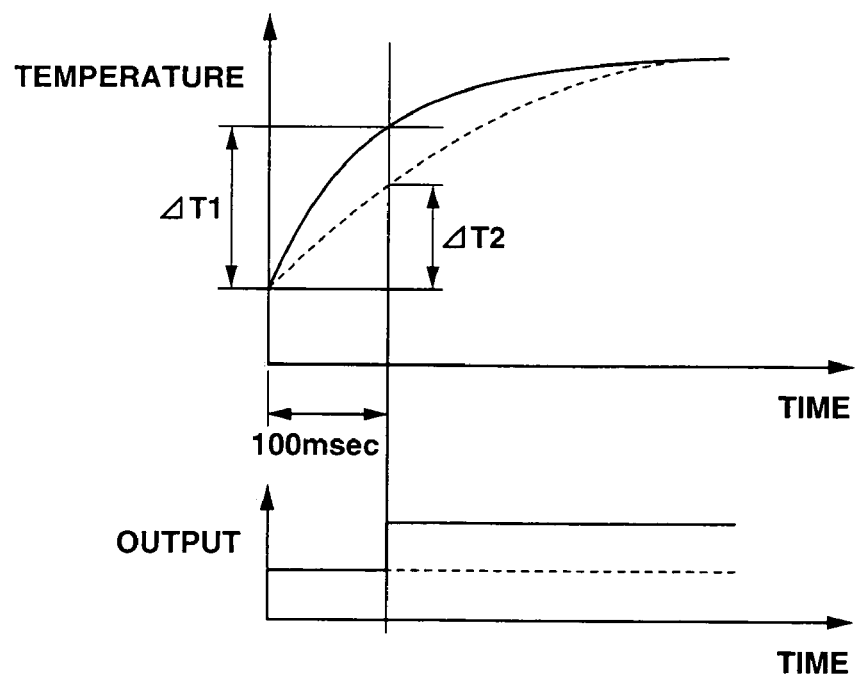
Figure 11:
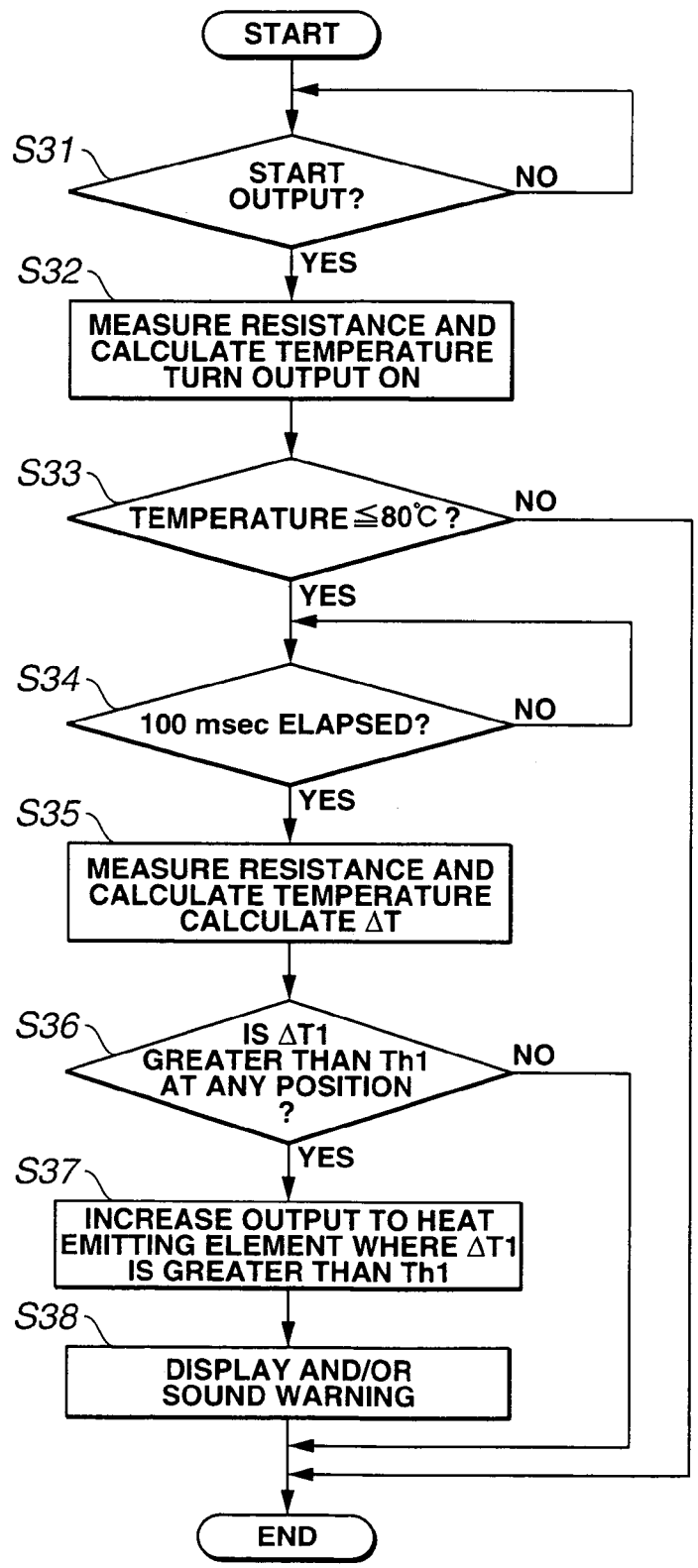

Next, the heat-emitting treatment device according to the fourth embodiment of the present invention will be described with reference to FIGS. 10 and 11. FIG. 10 is an explanatory diagram for describing the change in heat mission temperature of the heat-emitting elements of the heat-emitting treatment device according to the fourth embodiment of the present invention, and FIG. 11 is a flowchart illustrating the determination operations for a thermal connection state of the heat-emitting treatment unit by the main device unit.

The hardware configuration of the main device unit 3 according to the fourth embodiment is the same as that of the main device unit 3 according to the first embodiment, but the program for stipulating the control actions of the control unit 33 is different, and accordingly the processing actions are different.

The present embodiment is an arrangement wherein predetermined thermal coagulation/incision treatment can be performed even in the event that the connection between the heat-generating element 21 and the heat transmitting member 22 is not good.

In FIG. 10, the horizontal axis represents time, and the vertical axis represents the generated temperature of the heat-generating element 21, and the output of heat emission electric power.

In the event that the thermal connection of the heat-generating element 21 and the heat transmitting member 22 is good, the heat generated at the heat-generating element 21 is effectively conducted to the heat transmitting member 22 and dissipated, so a relatively gradual increase in temperature is exhibited, as indicated by the dotted line in FIG. 10, thereby enabling the temperature of heat transmitted to the body tissue via the heat transmitting member 22 to reach a predetermined temperature for a short time.

However, in the event that the thermal connection of the heat-generating element 21 and the heat transmitting member 22 is poor, the heat generated at the heat-generating element 21 is not effectively conducted to the heat transmitting member 22 so conduction and dissipation is inefficient, and in the event that the output of heat emission electric power is constant, a steep increase in temperature is exhibited, as indicated by the solid line in FIG. 10, but time is required for this heat to reach a predetermined temperature to be transmitted from the heat transmitting member 22 to the body tissue, so with the present embodiment, the output of the heat-emitting electric power is raised such that the temperature of the heat generated by the heat-generating element 21 is raised, thereby speeding up the time required for the heat, to be transmitted from the heat transmitting member 22 to the body tissue, to reach the predetermined temperature. The contents of the control operations of the control unit 33 of the device main unit 3 in the event that the thermal connection of the heat-generating element 21 and the heat transmitting member 22 is poor will now be described with reference to the flowchart of FIG. 11.

First, preparation for the coagulation/incision processing is performed, such as connecting the cable connector of the coagulation/incision forceps 2 to the forceps connector 15 of the device main unit 3, turning the electric power switch 10 on, setting the heat emission electric power value to be supplied to the heat-emitting treatment unit 7 of the coagulation/incision forceps 2 with the output settings switches 11, and so forth. Upon these preparations being completed, in step S31 the control unit 33 enters a standby state for input of instructions from the foot switch 6 to start output of heat emission electric power to the coagulation/incision forceps 2.

Upon the foot switch 6 being operated to instruct output of heat emission electric power, in step S32 the control unit 33 drives the temperature measuring units 32*a* through 32*c* to calculate the resistance value of the heat-generating elements 21*a* through 21*c* based on the minute electric power supplied to the heat-generating elements 21*a* through 21*c* from the output units 31*a* through 31*c*, and convert the resistance value into the temperature, thereby measuring the room temperature of each of the heat-generating elements 21*a* through 21*c* before starting coagulation/incision.

Upon the temperature measurement of the heat-generating elements 21*a* through 21*c* ending, the control unit 33 drives the output units 31*a* through 31*c* to supply heat emission electric power for coagulation and incision to each of the heat-generating elements 21*a* through 21*c*. Along with supplying of the heat emission electric power, the control unit 33 starts a time count of unshown timer functions for measuring time.

Next, in step S33, the control unit 33 determines whether or not the heat generation temperature of the heat-generating elements 21*a* through 21*c* measured in step S32 before starting coagulation/incision is equal to or lower than the standard temperature 80° C. In the event that the results of determination show that any one of the heat-generating elements 21*a* through 21*c* exceeds 80° C., this means that the effects of afterheat of the previous treatment are too great to determine the connection state, so the determining operations of the connection state between the heat-generating element 21 and heat transmitting member 22 are ended by the control unit 33.

In the event that the measured temperature before starting coagulation/incision is determined to be equal to or lower than 80° C. in step S33, the control unit 33 stands by in step S34 until 100 msec elapse on the timer count of the timer functions started at the time of starting the supply of heat emission electric power in step S32.

Following 100 msec elapsing on the timer count in step S34, in step S35 the control unit 33 drives the temperature measuring units 32*a* through 32*c* again, and measures the generated temperature of the heat-generating elements 21*a* through 21*c* by calculating the resistance value of the heat-generating elements 21*a* through 21*c* based on the voltage and current values of the heat emission electric power supplied to the heat-generating elements 21*a* through 21*c*, and converting the resistance value into heat generation temperature.

The difference $\Delta T$ between the heat generation temperature of the heat-generating elements 21*a* through 21*c* measured in step S35, and the heat generation temperature of each of the heat-generating elements 21*a* through 21*c* measured in step S32 before starting coagulation/incision, is calculated. That is to say, $\Delta T1$ or $\Delta T2$ in FIG. 10 is calculated.

Next, in step S36, the control unit 33 compares the heat generation temperature difference $\Delta T$ calculated in step S35 with a preset predetermined temperature difference Th1. In this step S36, in the event that the heat generation temperature differences $\Delta Ta$ thorough $\Delta Tc$ for each of the heat-generating elements 21*a* through 21*c* are all equal to or below the predetermined temperature difference Th1, the control unit 33 determines that the connection state between the heat-generating elements 21a through 21c and the heat transmitting member 22 is good, as indicated by the dotted line in FIG. 10, and the process of determining the thermal connecting state of the heat-generating element 21 and heat transmitting member 22 ends.

On the other hand, in the event that even one of the heat generation temperature differences ΔTa thorough ΔTc for the heat-generating elements 21a through 21c exceeds the predetermined temperature difference Th1, the control unit 33 determines that the connection state between the heat-generating elements 21a through 21c and the heat transmitting member 22 is not good, as indicated by the solid line in FIG. 10, and the control unit 33 controls driving of the output unit 31 to increase the output of the heat emission electric power, so as to improve the processing efficiency for coagulation/incision with the heat-generating element 21 which has a great heat generation temperature difference ΔT in step S37.

That is to say, even in the event that the temperature generated by the heat-generating element 21 is sufficient, the amount of heat transmitted is small or is delayed and the temperature is low unless the connection state between the heat-generating element 21 and the heat transmitting member 22 is good, leading to lower efficiency in coagulation/incision of the body tissue. Thus, with the present embodiment, the output of heat emission electric power to the heat-generating element 21 is increased to raise the temperature of the heat generated by the heat-generating element 21, thus compensating for deterioration in the coagulation/incision capabilities of the body tissue.

Next, in step S38, the control unit 33 notifies the technician of the poor thermal connecting state of the heat-generating element 21 and heat transmitting member 22 by driving the error display unit 13 on the main device unit 3 or driving an unshown warning sound emitting function, and the process of determining the thermal connecting state of the heat-generating element 21 and heat transmitting member 22 ends.

Thus, even in the event that a poor connection between the heat-generating element 21 and heat transmitting member 22 is detected in the processes of performing coagulation/incision treatment, the coagulation/incision can be continued.

Fifth Embodiment

Figure 13:
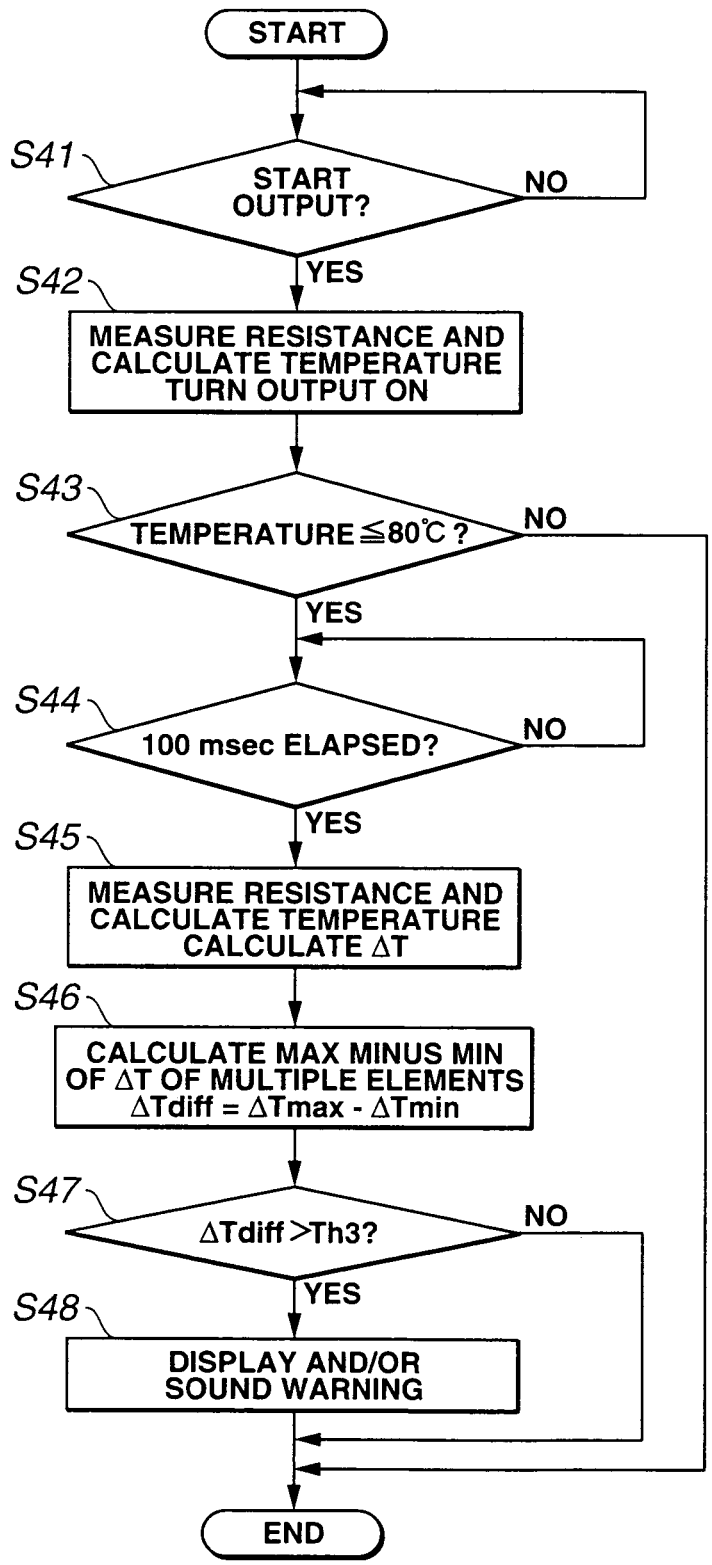

Next, the heat-emitting treatment device according to the fifth embodiment of the present invention will be described with reference to FIGS. 12A through 13. FIG. 12A is a block diagram illustrating the configuration of the main device unit 3B of the heat-emitting treatment device according to the fifth embodiment, FIG. 12B is an explanatory diagram for describing the change in heat mission temperature of the heat-emitting elements, and FIG. 13 is a flowchart illustrating the determination operations for thermal connection of the heat-emitting treatment unit by the main device unit.

The hardware configuration of the main device unit 3B according to the fifth embodiment shown in FIG. 12A is almost the same as that of the main device unit 3 according to the first embodiment, with the difference being the actions in processing by the control unit 33B. The control unit 33B has a CPU 33c for performing control operations, and the program data stipulating the control operations of the CPU 33c is stored in an EEPROM 33d serving as an electrically-rewritable non-volatile recording medium, for example.

Also, the control unit 33B is connected to a communication port 41 via a communication interface 40. A personal computer 42 (denoted by "PC" in FIG. 12A), for example, which is an external device from the device main unit 3B, is connected to the communication port 41, so that program data can be stored in the EEPROM 33d by being transmitted from the personal computer 42 to the CPU 33c. The CPU 33c follows the program data to carry out the later-described control operations shown in FIG. 13. Further, with the present embodiment, the program data stored in the EEPROM 33d can be easily updated.

Other hardware configurations are the same as that of the main device unit 3 according to the first embodiment, so the components will be denoted with the same reference numerals and description thereof will be omitted.

As with the arrangement described in the second embodiment, the forceps connector 15 has a connection detection unit 15a of the cable connector 5. Accordingly, as with the second embodiment, an arrangement may be made wherein, at the point that the coagulation/incision forceps 2 are connected to the main device unit 3B, automatic determining processing is performed regarding the connection state between the heat-generating element 21 and the heat transmitting member 22.

With the present embodiment, upon connecting the coagulation/incision forceps 2 to the main device unit 3B, the connection with the heat transmitting member 22 is determined based on the difference between the heat generation temperature of the multiple heat-generating elements 21a through 21c provided to the heat-emitting treatment unit 7 of the coagulation/incision forceps 2.

As with FIG. 4 described above, in FIG. 12B the horizontal axis represents time, and the vertical axis represents the generated temperature of the heat-generating element 21, thereby indicating the change in temperature upon supplying heat emission electric power to the heat-generating element 21 of the heat-emitting treatment unit 7 of the coagulation/incision forceps 2. This shows the change in temperature due to the thermal connection between the multiple heat-generating elements 21 (this description being a specific example involving three heat-generating elements 21a through 21c) provided to the heat-emitting treatment unit 7 of the coagulation/incision forceps 2, and the heat transmitting member 22. For example, the thermal connection of the heat-generating element 21a is not good, exhibiting a temperature rise such as shown by the solid line in FIG. 12B, and the thermal connections of the other two heat-generating elements 21b and 21c are good, exhibiting temperature rises such as shown by the dotted lines in FIG. 12B.

The operating procedures of the control unit 33B for determining the connection state of the multiple heat-generating elements 21a through 21c and the heat transmitting member 22 based on the difference of the heat generation temperature change, will be described with reference to the flowchart in FIG. 13. Upon the coagulation/incision forceps 2 being connected to the main device unit 3B and the electric power switch 10 of the main device unit 3B being turned on, and further upon preparation of coagulation/incision treatment such as setting the heat emission electric power values for the output to be supplied to the heat-emitting treatment unit 7 of the coagulation/incision forceps 2 by the output settings switches 11 being completed, the CPU 33c of the control unit 33B starts the control operations shown in FIG. 13.

Upon the foot switch 6 being operated in step S41, the CPU 33c of the control unit 33B enters a standby state awaiting input on instructions to supply heat emission electric power to the coagulation/incision forceps 2.

In the event that the foot switch 6 is operated and the there are instructions to output heat emission electric power, in step S42 the CPU 33c drives the temperature measuring units 32a through 32c to calculate the resistance value of the heat-generating elements 21a through 21c based on the minute electric power supplied to the heat-generating elements 21a through 21c from the output units 31a through 31c, and convert the resistance value into heat generation temperature, thereby measuring the room temperature of each of the heat-generating elements 21a through 21c before starting coagulation/incision.

Upon the temperature measurement of the heat-generating elements 21a through 21c ending, the CPU 33c drives the output units 31a through 31c to supply heat emission electric power for coagulation and incision to each of the heat-generating elements 21a through 21c. Along with supplying of the heat emission electric power, the control unit 33B starts a time count of unshown timer functions for measuring time.

Next, in step S43, the CPU 33c determines whether or not the heat generation temperature of the heat-generating elements 21a through 21c measured in step S42 before starting coagulation/incision is equal to or lower than the standard temperature 80° C. In the event that the results of determination show that any one of the heat-generating elements 21a through 21c exceeds 80° C., this means heat generation is caused due to a factor other than the connection state between the heat-generating element 21 and the heat transmitting member 22, so the determining operations of the connection state between the heat-generating element 21 and heat transmitting member 22 are ended.

In the event that the temperature measured in step S43 before starting coagulation/incision is determined to be equal to or lower than 80° C., in step S44 the CPU 33c stands by until 100 msec elapse on the timer count of the timer functions activated at the time of starting supplying heat emission electric power in step S42. Following 100 msec elapsing on the timer count in step S44, in step S45 the CPU 33c drives the temperature measuring units 32a through 32c again, and measures the generated temperature of the heat-generating elements 21a through 21c by calculating the resistance value of the heat-generating elements 21a through 21c based on the voltage and current values of heat emission electric power supplied to the heat-generating elements 21a through 21c, and converting the resistance value into temperature.

The CPU 33c then calculates the difference ΔT between the heat generation temperature of the heat-generating elements 21a through 21c measured in step S45, and the heat generation temperature of each of the heat-generating elements 21a through 21c measured in step S42 before starting coagulation or incision. That is to say, ΔTA through ΔTC in FIG. 10 are calculated.

Next, in step S46, the CPU 33c calculates the difference between the maximum value ΔTmax and minimum value ΔTmin of the temperature differences ΔTA through ΔTC of the heat-generating elements 21a through 21c calculated in step S45, i.e., calculates (ΔTdiff=ΔTmax−ΔTmin), and in step S47, compares the temperature difference ΔTdiff of the maximum value ΔTmax and minimum value ΔTmin calculated in step S46 with a preset predetermined temperature difference Th3. This predetermined temperature difference Th3 is a value experimentally obtained from various connecting states between the heat-generating element 21 and heat transmitting member 22, and serves as a reference value for determining whether or not the thermal connecting state of the heat-generating element 21 and heat transmitting member 22 is good.

In step S47, in the event that the generation temperature difference ΔTdiff of the heat-generating elements 21a through 21c is below the predetermined temperature difference Th3, the CPU 33c determines that the connection state between the heat-generating elements 21a through 21c and the heat transmitting member 22 is good, and the process of determining the thermal connecting state of the heat-generating element 21 and heat transmitting member 22 ends.

On the other hand, in the event the generation temperature difference ΔTdiff for the heat-generating elements 21a through 21c exceeds the predetermined temperature difference Th3, the CPU 33c determines that there is a heat-generating element, heat-generating element 21a for example, wherein the connection state with the heat transmitting member 22 is not good, as indicated by the solid line in FIG. 12B, and in step S48 notifies the technician of a poor thermal connecting state of the heat-generating element 21 and heat transmitting member 22 by driving the error display unit 13 on the main device unit 3B or driving an unshown warning sound emitting function, and the process of determining the thermal connecting state of the heat-generating element 21 and heat transmitting member 22 ends.

Note that while the fifth embodiment has been described as processing for determining the thermal connection between the heat-generating element 21 and heat transmitting member 22 at the point of starting supplying heat emission electric power from the foot switch 6, it is clear that this may be applied to operations for automatically determining the thermal connection between the heat-generating elements 21 and heat transmitting member 22 upon the coagulation/incision forceps 2 being connected to the main device unit 3B as with the second and third embodiments.

Thus, using the relative difference in temperature rise of the multiple heat-generating elements 21 enables poor or deteriorated thermal connecting between the heat-generating elements 21 and heat transmitting member 22 to be detected even for coagulation/incision forceps 2 with different thermal connection structures and means.

Sixth Embodiment

Figure 14:
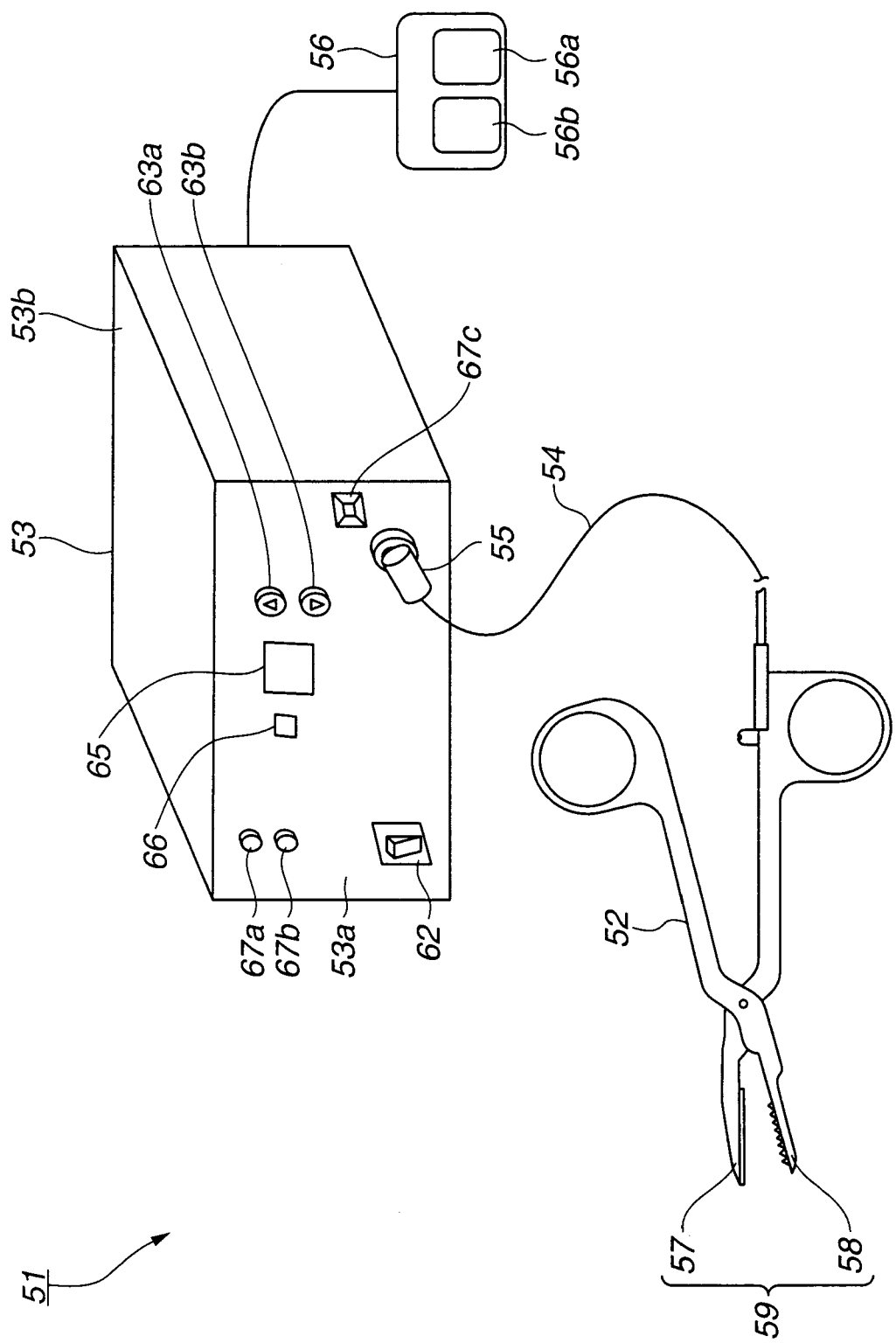

The heat-emitting treatment device according to the sixth embodiment of the present invention will be described with reference to FIGS. 14 through 22. As shown in FIG. 14, a heat-emitting treatment device 51 comprises coagulation/incision forceps 52, and a main device unit 53 for supplying heat-emitting electric power to the coagulation/incision forceps 52.

Figure 16:
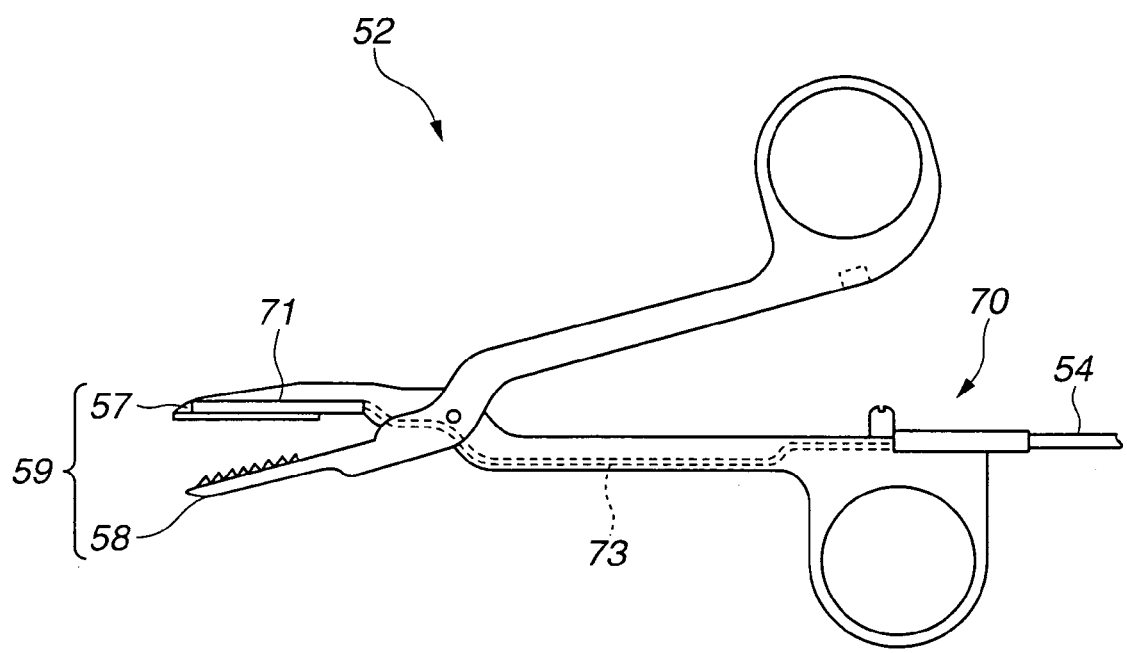

Also referring to FIG. 16, the coagulation/incision forceps 52 have a handle portion 70 at the base side thereof for the technician to hold and operate, and a treatment unit 59 at the tip side of the handle portion 70, comprising a heat-emitting treatment unit 57 for grasping the body tissue by operating the handle portion 70 and performing treatment with heat, and an elastic receiving unit 58. A heat-generating element 71 is provided on the heat-emitting treatment unit 57, with a lead 73 of a connecting cable 54 contained in the handle portion 70 being connected to the heat-generating element 71.

A connector 55 is provided at the base portion of the connoting cable 54, so as to be connected to the main device unit 53 such that heat emission electric power is supplied from the main device unit 53 to the heat-generating element 71 of the heat-emitting treatment unit 57.

Figure 15A:
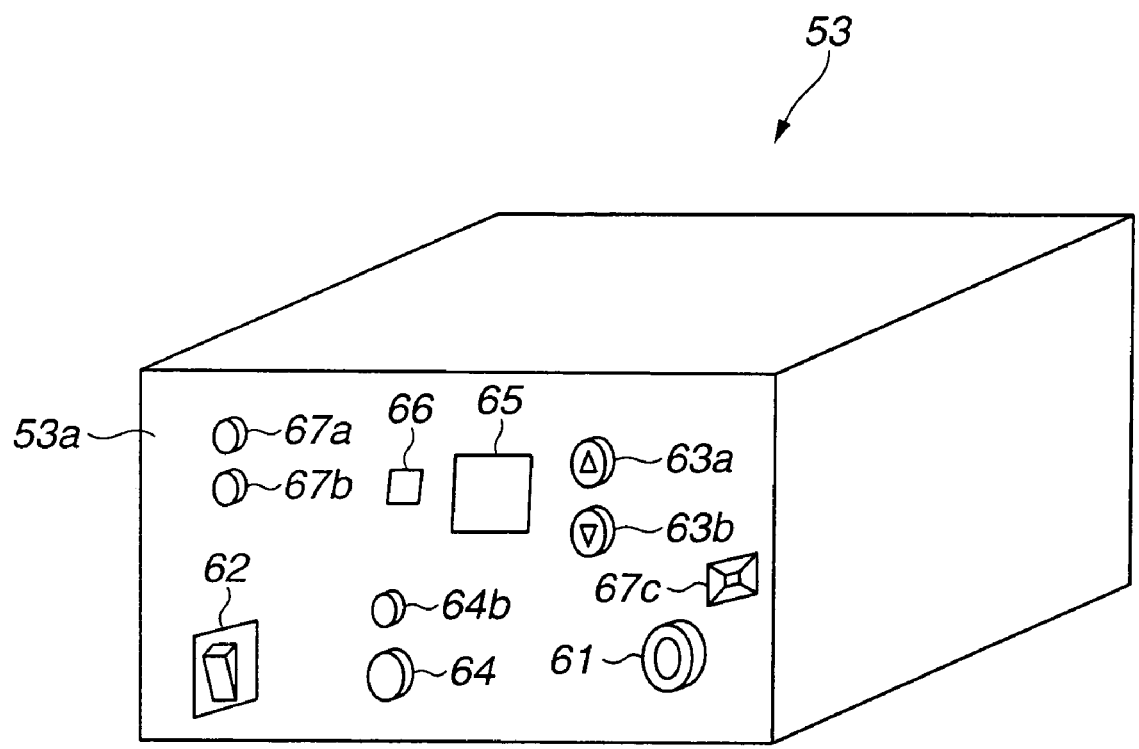
FIGS. 15A and 15B are respectively a frontal perspective view from the front panel side and a rear view from the rear panel side, of the main device unit of the heat-emitting treatment device.
Figure 15B:
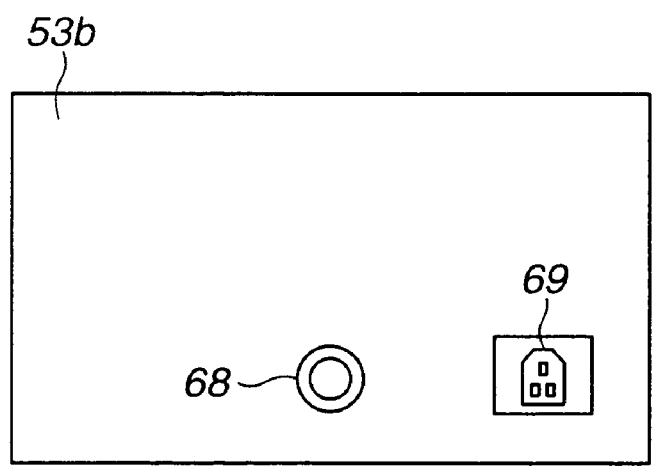

Referring to FIG. 15 as well, the device main unit 53 has a front panel 53a on which are provided a connector receptacle 61 to which the connector 55 of the coagulation/incision forceps 52 is connected, an electric power switch 62 for turning the power driving the device main unit 53 on and off, output settings switches 63 (comprising a temperature increasing switch 63a and a temperature decreasing switch 63b) for setting the heat generation temperature level of the heat-emitting treatment unit 57 of the coagulation/incision forceps 52, an output settings display unit 65 for displaying the heat generation temperature level set with the output settings switches 63, an output display unit 66 for displaying application of electricity to the coagulation/incision forceps 52 during the coagulation/incision treatment, an error display unit 67 (comprising an abnormal lamp display 67a for the coagulation/incision forceps 52, an abnormal lamp display 67b for internal means of the main device unit 53, and a warning sound buzzer 67c) used in the event that there is some abnormality in the heat-emitting treatment device 51, and so forth.

Also, provided to a rear panel 53b of the main device unit 53 is an electric power source socket 69 to which an electric power source plug of an electric power source cable for supplying driving electricity to the main device unit 53 is connected, and a foot switch connector 68 to which a foot switch 56 is connected for the operator to operate by foot, to control instructions of supplying electric power for heat emission to the coagulation/incision forceps 52 from the main device unit 53. The foot switch 56 comprises a maximum output switch 56a for instructing heating the coagulation/incision forceps 52 to the maximum level, and a set output switch 56b for instructing heating at a heat generation temperature level set with the output settings switches 63.

The main device unit 53 is capable of accepting connection of coagulation/incision forceps 52 with as many as four heat-generating elements 71 provided to the heat-emitting treatment unit 57, such that supply of heat emission electrical power from the main device unit 53 to each of the heat-generating elements 71, and determining the thermal connection state between the multiple heat-generating elements 71 and a later-described heat transmitting plate 72.

Figure 17A:
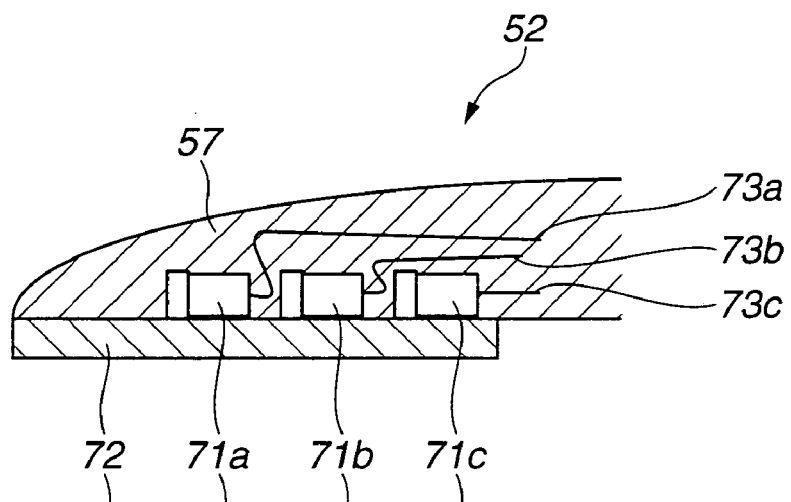
FIGS. 17A and 17B are respectively a cross-sectional view and a top perspective view of the heat-emitting treatment portion of the coagulation/incision forceps.
Figure 17B:
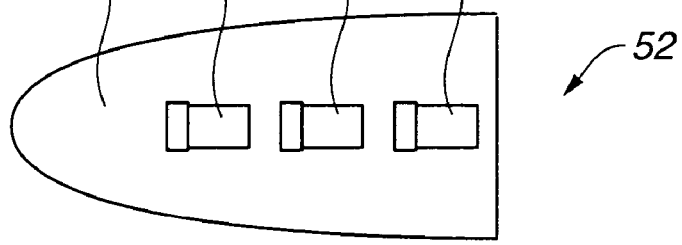
Figure 18A:
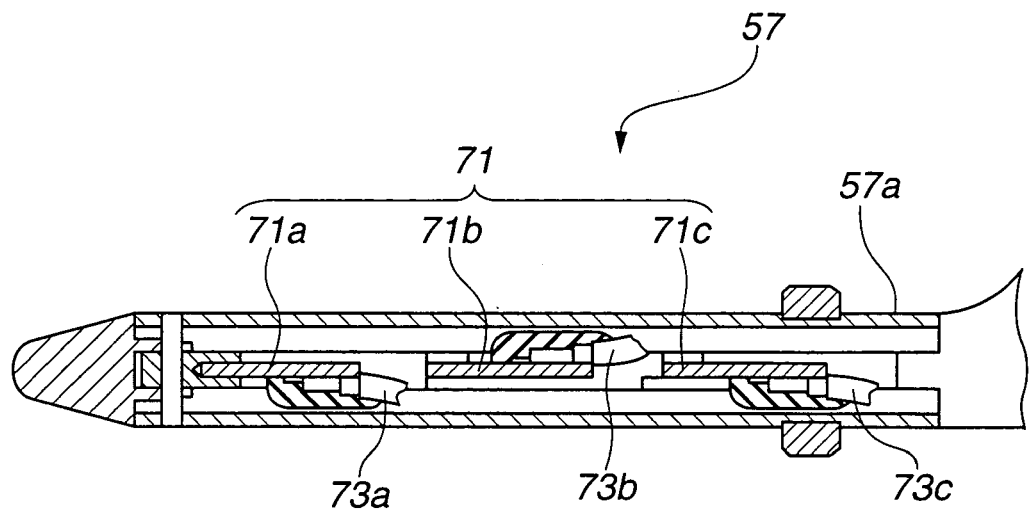
Figure 18B:
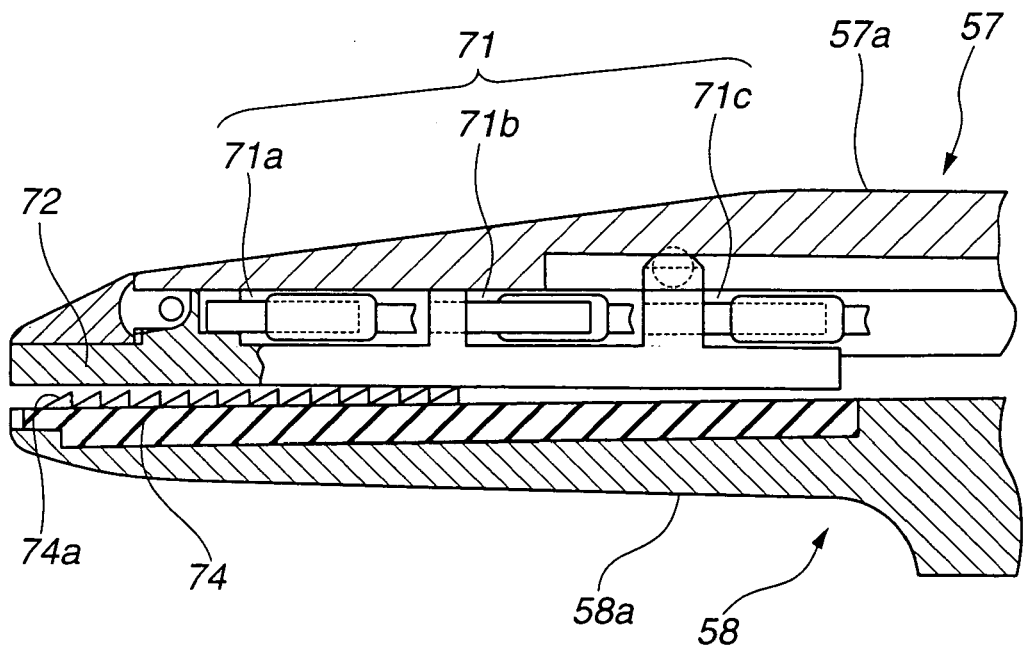

Next, the detailed configuration of a treatment unit 59 of the coagulation/incision forceps 52 will be described in detail with reference to FIGS. 17A through 18. Multiple heat-generating elements 71, for example three heat-generating elements 71a through 71c, are disposed within a heat-emitting treatment main unit 57a of the heat-emitting treatment unit 57 of the coagulation/incision forceps 52, and a heat transmitting plate 72, which is a plate-shaped heat transmitting member formed of a metal blade or the like for transmitting the heat of the heat-generating elements 71a through 71c to the body tissue so as to perform treatment by heating the body tissue, is provided on the elastic receiving unit 58 side.

The heat-generating elements 71a through 71c are thin-plate resistors formed on a ceramic substrate, for example, and leads 73a through 73c of the connecting cable 54 are connected to each of the heat-generating elements 71a through 71c. The heat-generating elements 71a through 71c are connected to one face of the heat transmitting plate 72 through a later-described transmitting member with excellent thermal conductivity, and the other face of the heat transmitting plate 72 is exposed to the elastic receiving unit 58 side.

That is to say, the heat-generating elements 71a through 71c and the heat transmitting plate 72 are thermally connected, such that the heat generated at the heat-generating elements 71a through 71c is transmitted to the heat transmitting plate 72.

On the other hand, the elastic receiving unit 58 comprises an elastic member 74 on the elastic receiving main unit 58a at the face opposing the heat transmitting plate 72 of the heat-emitting treatment unit 57, with non-slip formations 74a formed on the exposed surface thereof.

With the present embodiment, a technician can grasp a treatment portion of body tissue between the heat-emitting treatment unit 57 of the treatment unit 59 and the elastic receiving unit 58 by opening or closing the handle portion 70 of the coagulation/incision forceps 52, and transmit the heat generated by the heat-generating elements 71 to the body tissue grasped with the heat transmitting plate 72, thereby performing coagulation and incision treatment with this heat.

Figure 19:
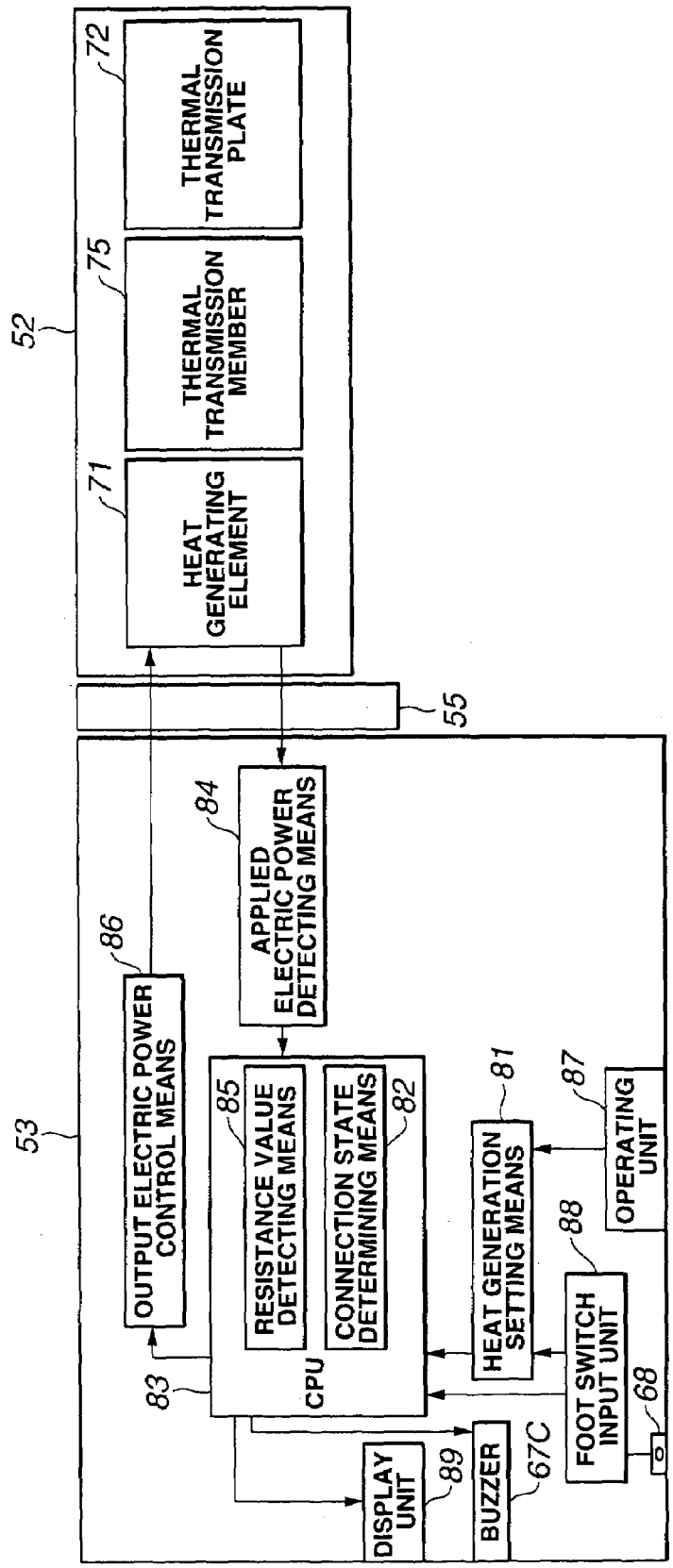

Next, the internal configuration of the device main unit 53 will be described with reference to FIG. 19. The heat-generating elements 71 and the heat transmitting plate 72 are connected with a transmitting material 75 such as solder or the like, in order to thermally connect the multiple heat-generating elements 71 to the heat transmitting plate 72, at the heat-emitting treatment unit 57 of the coagulation/incision forceps 52.

The device main unit 53 comprises a foot switch input unit 88 whereby operator instruction switch information from the foot switch 56 connected to the foot switch connector 68 is input, an operating unit 87 formed of the output settings switches 63, heat generation setting means 81 for setting the heat generation temperature level of the heat-generating elements 71 according to the operation input from the foot switch input unit 88 and operating unit 87, a microprocessor (hereafter, referred to simply as "CPU") 83 for controlling the driving of various means described later under the input of instructions to generate heat from the foot switch 88 and the heat generation temperature level set at the heat generation setting means 81, output electric power control means 86 for generating heat emission electric power via the connector 55 under the control of the CPU 83 for driving the heat generation of the heat-generating elements 71 of the coagulation/incision forceps 52, applied electric power detecting means 84 for detecting the electric power for heat generation applied to the heat-generating elements 71, a display unit 89 comprising an output settings display unit 65 for setting he temperature level of which driving is controlled by the CPU 83, an electricity output display unit 66 for indicating that electricity is being applied to the coagulation/incision forceps 52 and an abnormality display unit 67, and a buzzer 67c for emitting a warning sound.

Note that resistance value detecting means 85 for calculating the resistance values of the heat-generating elements 71 from the voltage value and current value of the heat emission electric power applied to the heat-generating elements 71 that has been detected by the applied electric power detecting means 84, and detecting the heat generation temperature of the heat-generating elements 71 from the calculated resistance values, connection state determining means 82 for determining the thermal connection state between the heat-generating elements 71 and the heat transmitting plate 72 from the heat emission electric power supplied to the heat-generating elements 71 that has been detected by the applied electric power detecting means 84, and various other driving control means, are built into the CPU 83.

Further, the main device unit 53 has an unshown electric power source for driving the main device unit 53, and for generating the heat emission electric power to be supplied from the output electric power control means 86 to the heat-generating elements 71.

With the heat-emitting treatment device 51 having such a configuration, upon a heat generation temperature level being input from the operating unit 87, the heat generation temperature level information is sent from the heat generation setting means 81 to the CPU 83, which drives the display unit 89 so as to display that heat generation temperature level. Now, with the heat generation temperature level having been set, turning the set output switch 56b of the foot switch 56 on causes the CPU 83 to drive the output electric power control means 86, thereby driving the heat-generating elements 71 so as to heat to the set heat generation temperature level.

The heat emission electric power supplied to the heat-generating elements 71 from the output electric power control means 86 is detected by the applied electric power detecting means 84, and the resistance value detecting means 85 calculates the resistance value of the heat-generating elements 71 from the detected voltage value and current value of the heat emission electric power.

The resistance values of the heat-generating elements 71 have a predetermined relation with change in the heat generation temperature, so the heat generation temperature of the heat-generating elements 71 is calculated by conversion from the resistance values of the heat-generating elements 71 calculated by the resistance value detecting means 85, and the heat emission electric power supplied to the heat-generating elements 71 from the output electric power control means 86 is controlled.

Also, the thermal connection state of the heat-generating elements 71 and the heat transmitting plate 72 is determined by the connection state determining means 82 from the heat emission electric power detected by the applied electric power detecting means 84, and in the event that the thermal connection state is not good, the CPU 83 drives the display unit 89 or the buzzer 67c to notify the technician with displays or warning sounds.

Figure 20:
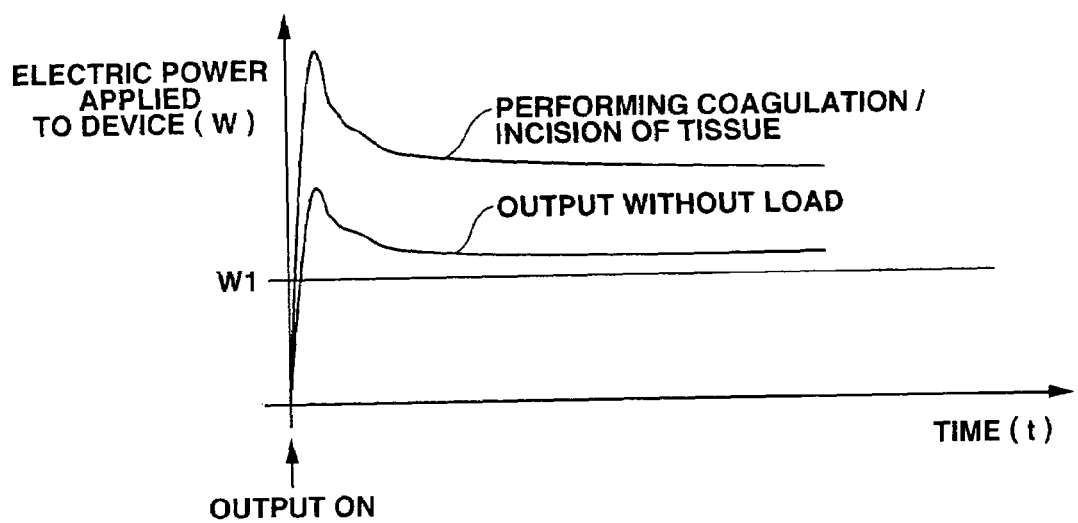
Figure 21:
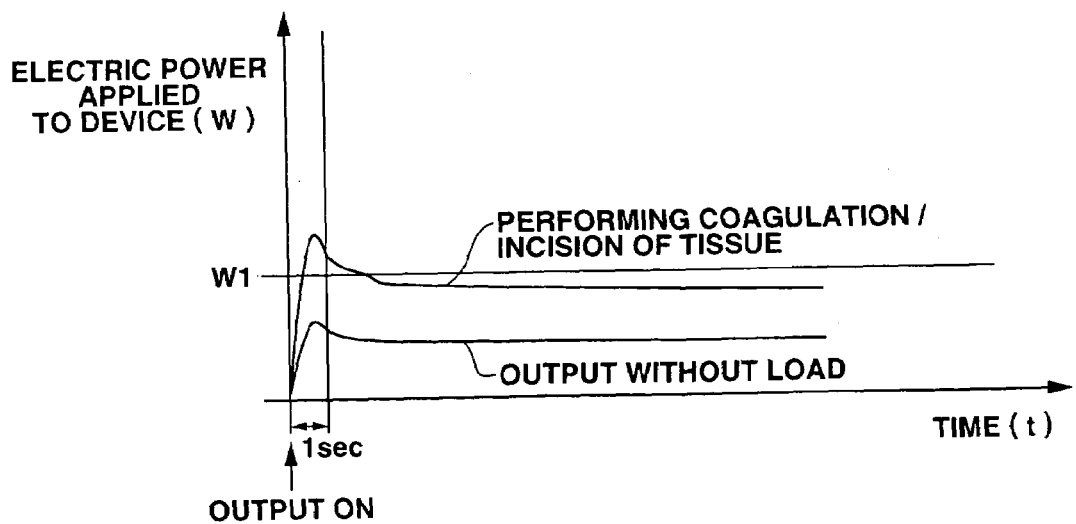

The determination of the thermal connection between the heat-generating elements 71 and the heat transmitting plate 72 will be described with reference to FIGS. 20 and 21. FIGS. 20 and 21 illustrate the relation between the passage of time and the electricity applied to the elements when hat emission electric power is applied to the heat-generating elements 71, and in the event that the thermal connection between the heat-generating elements 71 and the heat transmitting plate 72 is good, heat emission electric power is supplied such that the heat-generating elements 71 exhibit a set resistance value, i.e., reach a set temperature, as shown in FIG. 20.

At this time, in a state wherein no body tissue is held by the treatment unit 59 of the coagulation/incision forceps 52 and no coagulation or incision of tissue is performed thereby (hereafter referred to as operating "without load"), the heat-generating elements 71 of the coagulation/incision forceps 52 themselves make up a load as viewed from the output electric power control means 86, and also there is the need to heat the heat transmitting plate 72 to a desired temperature to prepare for coagulation/incision treatment, so the minimum application electricity for this preparatory heating is supplied thereto. In the drawings, W1 represents the threshold value of the minimum application electricity for operating without load.

On the other hand, in the event of body tissue being held by the treatment unit 59 of the coagulation/incision forceps 52 and heated, electric power is applied thereto for heating to the set temperature so as to apply heat and perform treatment on the body tissue, as indicated by the "coagulation/incision of tissue" curve in FIG. 20.

Next, in the event that the thermal connection state of the heat-generating elements 71 and the heat transmitting plate 72 is not good, and there is a soldering defect in the solder which is the transmitting material 75, the load on the heat-generating elements 71 is smaller than normal, as indicated in FIG. 21. Further, when operating without load, this is even lower, and drops below the threshold value W1 which is the minimum application electricity for normal connection. That is to say, in the event that the applied electric power is lower than the minimum application electricity threshold W1 for normal thermal connection between the heat-generating elements 71 and the heat transmitting plate 72, a defect in the connection state can be detected.

Figure 22:
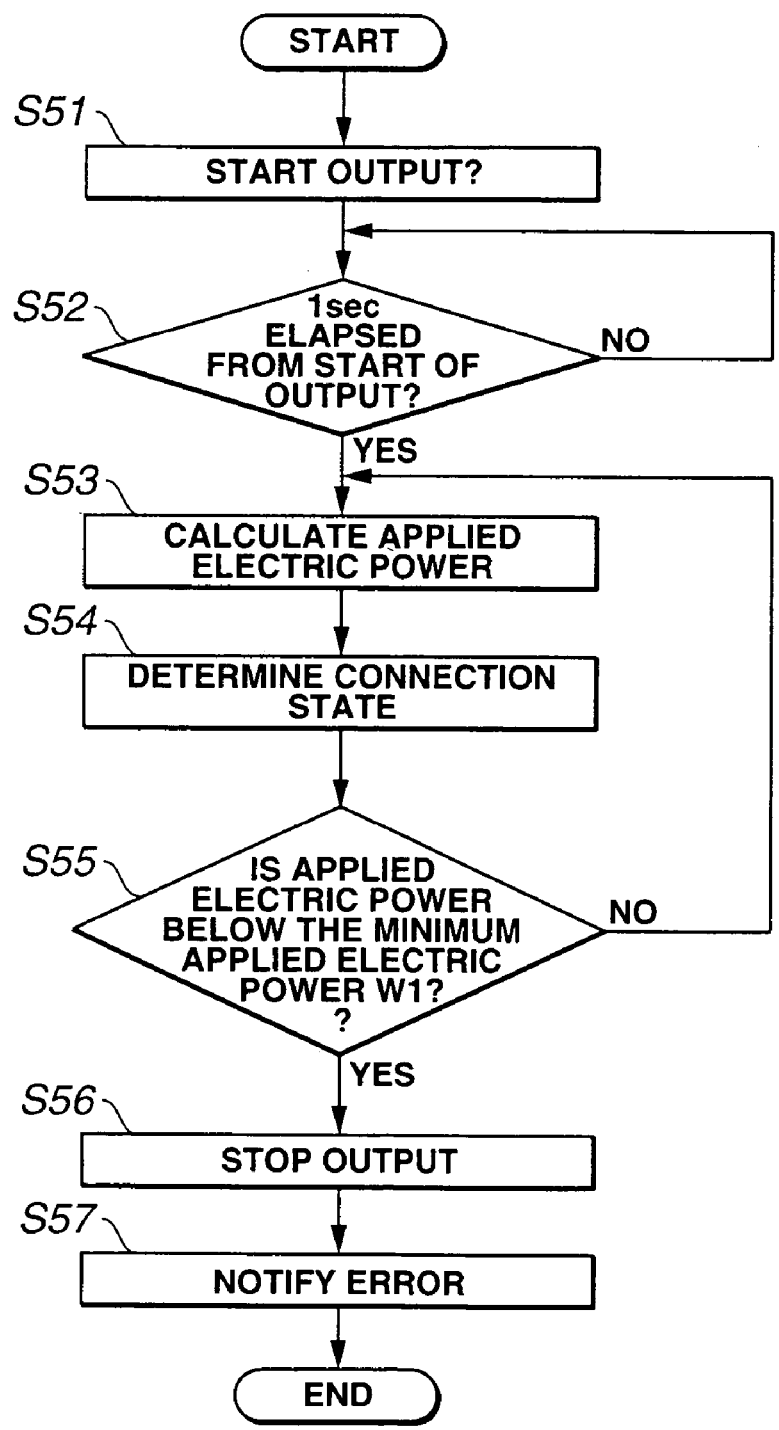

Now, FIG. 22 which is a flowchart relating to the actions for determining the connection state of the heat-generating elements 71 and the heat transmitting plate 72 will be described. This process takes advantage of the above-described phenomenon which allows the thermal connection state of the heat-generating elements 71 and the heat transmitting plate 72 to be determined according to the electric power supplied to the heat-generating elements 71.

In step S51, the CPU 83 controls driving of the output electric power control means 86 to start supply of the heat emission electric power for the predetermined heat generation temperature to the heat-generating elements 71. After starting supply of the heat emission electric power, the CPU 83 measures the elapsed time from the start of output, and stands by in step S52 until a predetermined period, 1 second for example, elapses.

Upon the predetermined period elapsing in the standby state in step S52, the CPU 83 in the next step S53 calculates the applied electric power from the voltage value and the current value of the electricity applied to the heat-generating elements 71, detected by the applied electric power detecting means 84.

Next, in step S54, the CPU 83 drives the connection state determining means 82 to determine the thermal connection state of the heat-generating elements 71 and the heat transmitting plate 72 based on the electric power applied to the heat-generating elements 71 which has been detected by the applied electric power detecting means 84.

In the following step S55, the CPU 83 receives the results of the determination, and determines whether or not the electric power applied to the heat-generating elements 71 is lower than the minimum application electricity threshold W1. In the event that the electric power applied to the heat-generating elements 71 is higher than the minimum application electricity threshold W1, the flow returns to step S53, and continues calculation of the electric power applied to the heat-generating elements 71 and determining of the level of the applied electric power.

In the event that the electric power applied to the heat-generating elements 71 is determined to be lower than the minimum application electricity threshold W1 in step S55, in the subsequent step S56, the CPU 83 stops output of the heat emission electric power being supplied to the heat-generating elements 71 from the output electric power control means 86.

In the following step S57, the CPU 83 drives the display unit 89 and the buzzer 67c, so as to notify the technician that the thermal connection state between the heat-generating elements 71 and the heat transmitting plate 72 is not good.

As shown in FIGS. 20 and 21, the applied electric power immediately after starting supply exhibits a maximum value for a short time, and then settles to a stable level. The reason for the standby time of a predetermined period in step S52 is to determine the thermal connection state in this stable state.

As described above, the state of the transmitting material 75 thermally connecting the heat-generating elements 71 and the heat transmitting plate 72 can be constantly monitored while the body tissue is being heated, based on the heat emission electric power being supplied to the heat-generating elements 71, and in the event that the thermal connection deteriorates and good thermal connection is lost, the technician can be speedily notified and the heat emission electric power being supplied to the heat-generating elements 71 can be stopped.

Figure 23:
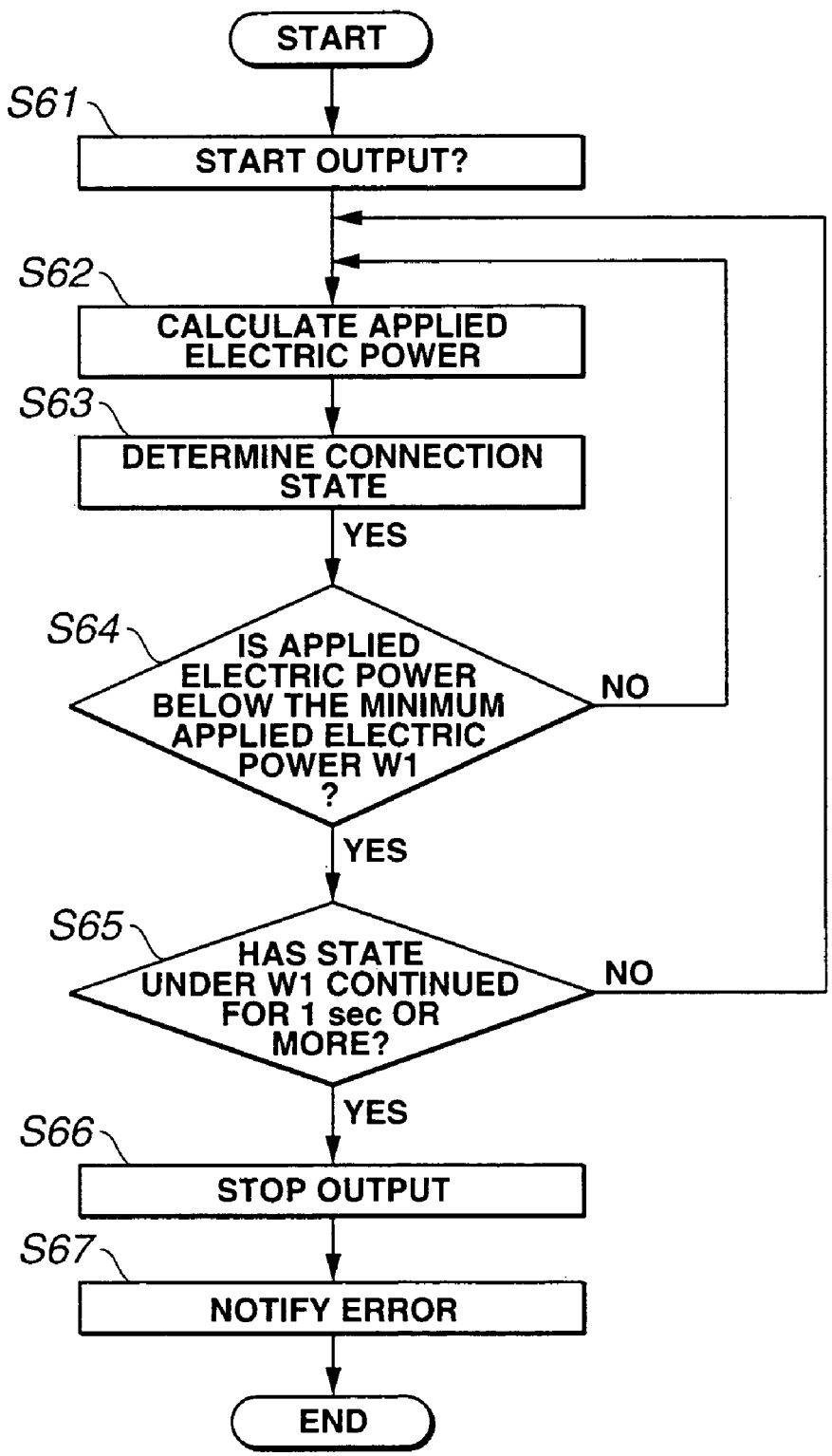

Next, a modification of the heat-emitting treatment device will be described with reference to FIG. 23. The configuration of the modification of the heat-emitting treatment device is the same as that of the sixth embodiment, with the difference being the processing for determining the state of the transmitting material 75 thermally connecting the heat-generating elements 71 and the heat transmitting plate 72.

In step S61, upon heat treatment driving being started with the foot switch 56, the CPU 83 controls driving of the output electric power control means 86 to start supply of the heat emission electric power for the predetermined heat generation temperature, input from the operating unit 87 to the heat generation setting means 81, to the heat-generating elements 71.

Next, in step S62, the CPU 83 detects the voltage value and the current value of the electricity applied to the heat-generating elements 71 with the applied electric power detecting means 84, and calculates the applied electric power from the detected voltage value and current value.

In step S63, the CPU 83 drives the connection state determining means 82 to determine the thermal connection state of the heat-generating elements 71 and the heat transmitting plate 72 based on the applied electric power calculated in step S62. The CPU 83 receives the determination results, and in the subsequent step S64, determines whether or not the electric power applied to the heat-generating elements 71 is lower than the minimum application electricity threshold W1. In the event that the electric power applied to the heat-generating elements 71 is determined to be higher than the minimum application electricity threshold W1, the flow returns to step S62, and continues detection and monitoring of the electric power applied to the heat-generating elements 71.

In the event that the applied electric power is determined to be lower than the minimum application electricity threshold W1 in step S64, in the subsequent step S65 the CPU 83 determines whether or not the supply of electric power to the heat-generating elements 71 has been in a state lower than the minimum application electricity threshold W1 for a predetermined period or longer, e.g., for one second or longer.

Now, the reason that the one second period or longer is applied is that there is a time span wherein the supply of electric power is lower than the minimum application electricity threshold W1 between starting of output and reaching the maximum applied electric power, and the one second period is for removing this time span from the measurements.

In the event that the supply of electric power has not been in a state lower than the minimum application electricity threshold W1 for the predetermined one second or longer, the flow returns to step S62 and repeats the applied electric power detecting, and in the event that the supply of electric power has been in a state lower than the minimum application electricity threshold W1 for the predetermined one second or longer, the CPU 83 determines that the state of the transmitting material 75 thermally connecting the heat-generating elements 71 and the heat transmitting plate 72 is not good, so the CPU 83 stops the driving of the output electric power control means 86 in step S66, stops the supply of heat emission electric power to the heat-generating elements 71, and drives the display unit 89 and the buzzer 67c in step S67, so as to notify the technician that the thermal connection state of the transmitting material 75 is not good.

That is to say, with this arrangement, in the event that the supply of electric power to the heat-generating elements 71 is in a state lower than the minimum application electricity threshold W1 for the a predetermined period (one second for example) or longer, determination is made that the thermal connection state is faulty.

Thus, the state of the thermal connection of the heat-emitting treatment unit 57 of the coagulation/incision forceps 52 can be constantly monitored while the body tissue is being heated, and in the event that the thermal connection deteriorates, the technician can be speedily notified and the heating can be stopped.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A heat-emitting treatment device comprising:
   heater elements for emitting heat to treat body tissue;
   an electric power supplying circuit for supplying electric power so that the heater elements emit heat;
   a heat-transmitting member connected with the heater elements so as to provide the heat from the heater elements, heated by supplying electric power thereto, to the body tissue; and
   a determining device for determining the heat connection state of the heater elements and the heat-transmitting member;
   wherein the determining device is configured for detecting an amount of change in a temperature during a predetermined period of time of the heater elements, determining the heat connection state of the heater elements and the heat transmitting member, and comparing the detected amount of change in a temperature and a preset threshold value.

2. A heat-emitting treatment device according to claim 1, further comprising a control circuit for controlling the electric power supplying circuit, based on the determination results of the determining device.

3. A heat-emitting treatment device according to claim 1, further comprising a notification circuit for notifying, based on the determination results of the determining device.

4. A heat-emitting treatment device according to claim 1, wherein the determining device detects the amount of change in the temperature during a predetermined period of time of the heater elements based on the electric power supplied from the electric power supplying circuit to the heater elements.

5. A heat-emitting treatment device according to claim 1, further comprising a conditions determining device for determining whether or not conditions enabling determination of the connection state are satisfied.

6. A heat-emitting treatment device according to claim 4, wherein the determining device determines the thermal connection state between the heater elements and the heat-transmitting member, by comparing a value of the electric power supplied to the heater element with a preset threshold value.

7. A heat-emitting treatment device according to claim 4, wherein the determining device determines the thermal connection state between the heater elements and the heat-transmitting member, by comparing a value of the electric power supplied to the heater element following a predetermined time period elapsing from starting output from the electric power supplying circuit, with a preset threshold value.

8. A heat-emitting treatment device according to claim 1, wherein the determining device determines the thermal connection state between the heater elements and the heat-transmitting member, based on the change in temperature of the heater elements from the start of output from the electric power supplying circuit.

9. A heat-emitting treatment device according to claim 1, wherein the determining device determines the thermal connection state between the heater elements and the heat-transmitting member, based on the change in temperature of the heater elements after ending output from the electric power supplying circuit.

10. A heat-emitting treatment device according to claim 1, wherein the determining device determines the thermal connection state between the heater elements and the heat-transmitting member, based on the rate of change in temperature among the heater elements.

11. A heat-emitting treatment device according to claim 1, wherein the determining device detects the amount of change in the temperature during a predetermined period of time of the heater elements based on the change in resistance of the heater elements.

12. A heat-emitting treatment device according to claim 2, wherein, in the event that the determination results from the determining device show that the connecting state is low, the control circuit effects control such that the electric power supplied from the electric power supply circuit is increased.

13. A heat-emitting treatment device according to claim 1, further comprising a control circuit for determining the temperature of the heater elements before determining the connection state with the determining device.

14. A heat-emitting treatment device according to claim 13, wherein the control circuit determines the temperature under a weak electric power supply.

15. A heat-emitting treatment device according to claim 1, wherein the heater elements and heat transmitting member are provided on a treatment instrument, with a connector of the treatment instrument comprising a detection circuit for detecting the connection or non-connection to a connector receptacle of the main device unit where the electric power supply circuit is provided.

16. A heat-emitting treatment device according to claim 15, wherein determining actions of the connection state by the determining device are activated by the results of detecting connection by the detecting circuit.

17. A control method for a heat-emitting treatment device comprising heater elements for emitting heat to treat body tissue and a heat-transmitting member for transmitting heat from the heater elements to body tissue, the method comprising:
   an electric power supplying step for supplying electric power so that the heater elements emit heat;
   a determining step for detecting an amount of change in a temperature during a predetermined period of time of the heater elements and determining the connection state of the heater elements and the heat-transmitting member by comparing the detected amount of change in a temperature and a preset threshold value; and
   an electric power changing step for changing the electric power supplied, based on the determination results of the determining step.

18. A control method for a heat-emitting treatment device according to claim 17, wherein in the determining step, a thermal connection state between the heater elements and the heat-transmitting member is determined based on the electric power supplied to heat the heater elements.

19. A control method for a heat-emitting treatment device according to claim 18, wherein in the determining step, a thermal connection state between the heater elements and the heat-transmitting member is determined, based on the change in temperature of the heater elements from the start of the electric power supplying to heat the heater elements.

20. A control method for a heat-emitting treatment device according to claim 18, wherein in the determining step, a thermal connection state between the heater elements and the heat-transmitting member is determined, based on the change in temperature of the heater elements after ending of the electric power supplying to heat the heater elements.

21. A control method for a heat-emitting treatment device according to claim 17, wherein in the determining step, a thermal connection state between the heater elements and the heat-transmitting member is determined, based on the change in resistance of the heater elements.

22. A control method for a heat-emitting treatment device comprising heater elements for emitting heat to treat body tissue and a heat-transmitting member for transmitting heat from the heater elements to body tissue, the method comprising:
   an electric power supplying step for supplying electric power so that the heater elements emit heat;
   a determining step for detecting an amount of change in a temperature during a predetermined period of time of the heater elements and determining the connection state of the heater elements and the heat-transmitting member by comparing the detected amount of change in a temperature and a preset threshold value; and
   a notifying step for notifying, based on the determination results of the determining step.

23. A control method for a heat-emitting treatment device according to claim 22, wherein in the determining step, a thermal connection state between the heater elements and the heat-transmitting member is determined based on the electric power supplied to heat the heater elements.

24. A control method for a heat-emitting treatment device according to claim 23, wherein in the determining step, a thermal connection state between the heater elements and the heat-transmitting member is determined, based on the change in temperature of the heater elements from the start of the electric power supplying to heat the heater elements.

25. A control method for a heat-emitting treatment device according to claim 23, wherein in the determining step, a thermal connection state between the heater elements and the heat-transmitting member is determined, based on the change in temperature of the heater elements after ending of the electric power supplying to heat the heater elements.

26. A control method for a heat-emitting treatment device according to claim 22, wherein in the determining step, a thermal connection state between the heater elements and the heat-transmitting member is determined, based on the change in resistance of the heater elements.

27. A program storage device readable by a machine, tangibly embodying a program of instructions executable by the machine to perform method steps for controlling a heat-emitting treatment device comprising heater elements for emitting heat to treat body tissue and a heat-transmitting member for transmitting heat from the heater elements to body tissue, method steps including the steps of:

supplying electric power so that the heater elements emit heat;

detecting an amount of change in a temperature during a predetermined period of time of the heater elements; and determining the connection state of the heater elements and the heat-transmitting member by comparing the detected amount of change in a temperature and a preset threshold value.

28. The program storage device readable by a machine, tangibly embodying a program of instructions according to claim 27, further including the step of changing the electric power supplied, based on the determination results of the determining step.

29. The program storage device readable by a machine, tangibly embodying a program of instructions according to claim 27, further including the step of notifying, based on the determination results of the determining step.

* * * * *